(12) United States Patent
Meyerson et al.

(10) Patent No.: US 10,744,372 B2
(45) Date of Patent: Aug. 18, 2020

(54) BEHAVIOR DOMINATED SEARCH IN EVOLUTIONARY SEARCH SYSTEMS

(71) Applicant: Cognizant Technology Solutions U.S. Corporation, College Station, TX (US)

(72) Inventors: Elliot Meyerson, San Francisco, CA (US); Risto Miikkulainen, Stanford, CA (US)

(73) Assignee: Cognizant Technology Solutions U.S. Corporation, College Station, TX (US)

( * ) Notice: Subject to any disclaimer, the term of this patent is extended or adjusted under 35 U.S.C. 154(b) by 250 days.

(21) Appl. No.: 15/912,475

(22) Filed: Mar. 5, 2018

(65) Prior Publication Data
US 2018/0250554 A1 Sep. 6, 2018

Related U.S. Application Data

(60) Provisional application No. 62/467,061, filed on Mar. 3, 2017.

(51) Int. Cl.
*A63B 24/00* (2006.01)
*G06F 17/30* (2006.01)
(Continued)

(52) U.S. Cl.
CPC .......... *A63B 24/0062* (2013.01); *G06F 16/23* (2019.01); *G16H 20/30* (2018.01);
(Continued)

(58) Field of Classification Search
CPC ........ A63B 24/0062; A63B 2024/0065; A63B 2024/0068; G16H 20/30; G06T 16/23
See application file for complete search history.

(56) References Cited

U.S. PATENT DOCUMENTS 5,845,266 A * 12/1998 Lupien .................. G06Q 40/00
705/36 R
5,920,848 A * 7/1999 Schutzer ................ G06Q 20/10
705/33
(Continued)

FOREIGN PATENT DOCUMENTS

EP    2422276 A1    2/2012
EP    2422278 A1    2/2012
(Continued)

OTHER PUBLICATIONS

Koza, "Genetic Programming: On the Programming of Computers by Means of Natural Selection", Dec. 1992, MIT Press, pp. 1-609.
(Continued)

*Primary Examiner* — David L Leweis
*Assistant Examiner* — Matthew D Hoel
(74) *Attorney, Agent, or Firm* — Dawn-Marie Bey; Bey & Cotropia PLLC

(57) ABSTRACT

Roughly described, a computer system uses a behavior-driven algorithm that is better able to find optimum solutions to a problem by balancing the use of fitness and novelty measures in evolutionary optimization. In competition among candidate individuals, a domination estimate between a pair of individuals is determined by both their fitness estimate difference and their behavior difference relative to one another. An increase in the fitness estimate difference of one individual of the pair over the other increases the domination estimate of the first individual. An increase in the behavior distance between the pair of individuals decreases the domination estimate of both of the individuals. Individuals with a higher domination estimate are more likely to survive competitions among the candidate individuals.

18 Claims, 11 Drawing Sheets

(51) Int. Cl.
    *G06F 16/23* (2019.01)
    *G16H 20/30* (2018.01)
(52) U.S. Cl.
    CPC ............. *A63B 2024/0065* (2013.01); *A63B 2024/0068* (2013.01)

(56) References Cited

U.S. PATENT DOCUMENTS

| | | | | |
|---|---|---|---|---|
| 6,240,399 B1* | 5/2001 | Frank | ............... | G06Q 40/04 705/36 R |
| 6,249,783 B1* | 6/2001 | Crone | ............... | G06F 16/24553 |
| 7,013,344 B2* | 3/2006 | Megiddo | ............... | G06F 9/5066 709/213 |
| 7,370,013 B1* | 5/2008 | Aziz | ............... | G06F 9/5072 705/40 |
| 7,444,309 B2* | 10/2008 | Branke | ............... | G06N 3/126 706/13 |
| 8,527,433 B2* | 9/2013 | Hodjat | ............... | G06N 3/126 706/12 |
| 8,768,811 B2* | 7/2014 | Hodjat | ............... | G06N 3/126 705/36 R |
| 8,825,560 B2* | 9/2014 | Hodjat | ............... | G06N 3/126 706/10 |
| 8,909,570 B1* | 12/2014 | Hodjat | ............... | G06N 3/126 706/13 |
| 8,918,349 B2* | 12/2014 | Hodjat | ............... | G06N 3/126 706/12 |
| 8,977,581 B1* | 3/2015 | Hodjat | ............... | G06N 3/126 706/13 |
| 9,002,759 B2* | 4/2015 | Hodjat | ............... | G06N 3/126 706/13 |
| 9,466,023 B1* | 10/2016 | Shahrzad | ............... | G06N 3/086 |
| 2002/0019844 A1* | 2/2002 | Kurowski | ............... | H04L 67/42 709/201 |
| 2002/0080169 A1* | 6/2002 | Diederiks | ............... | H04N 21/4662 715/744 |
| 2004/0210545 A1* | 10/2004 | Branke | ............... | G06N 3/126 706/45 |
| 2004/0254901 A1* | 12/2004 | Bonabeau | ............... | G06N 3/126 706/13 |
| 2005/0033672 A1* | 2/2005 | Lasry | ............... | G06Q 40/00 705/35 |
| 2005/0187848 A1* | 8/2005 | Bonissone | ............... | G06Q 40/06 705/36 R |
| 2005/0198103 A1* | 9/2005 | Ching | ............... | G06Q 10/10 709/200 |
| 2007/0143198 A1* | 6/2007 | Brandes | ............... | G06Q 10/04 705/36 R |
| 2007/0143759 A1* | 6/2007 | Ozgur | ............... | G06F 9/5033 718/102 |
| 2007/0185990 A1* | 8/2007 | Ono | ............... | G06F 11/3452 709/224 |
| 2008/0071588 A1* | 3/2008 | Eder | ............... | G06Q 10/06 705/7.31 |
| 2008/0228644 A1* | 9/2008 | Birkestrand | ............... | G06Q 20/102 705/40 |
| 2009/0125370 A1* | 5/2009 | Blondeau | ............... | G06N 3/126 705/7.27 |
| 2009/0307638 A1* | 12/2009 | McConaghy | ............... | G06F 30/36 716/104 |
| 2010/0030720 A1* | 2/2010 | Stephens | ............... | G06Q 40/06 706/52 |
| 2010/0182935 A1* | 7/2010 | David | ............... | G06F 15/173 370/254 |
| 2010/0274736 A1* | 10/2010 | Hodjat | ............... | G06Q 40/04 705/36 R |
| 2010/0274742 A1* | 10/2010 | Hodjat | ............... | G06N 20/00 706/10 |
| 2010/0293119 A1* | 11/2010 | Ferringer | ............... | G06N 3/086 706/13 |
| 2011/0161264 A1* | 6/2011 | Cantin | ............... | G06N 3/126 706/13 |
| 2011/0246834 A1* | 10/2011 | Rajashekara | ............... | G06F 11/3676 714/38.1 |
| 2012/0239517 A1* | 9/2012 | Blondeau | ............... | G06N 3/126 705/26.1 |
| 2013/0124440 A1* | 5/2013 | Hodjat | ............... | G06N 3/126 706/13 |
| 2013/0254142 A1* | 9/2013 | Hodjat | ............... | G06N 20/00 706/12 |
| 2014/0006316 A1* | 1/2014 | Hodjat | ............... | G06Q 30/02 706/10 |
| 2014/0229362 A1* | 8/2014 | Hodjat | ............... | G06N 3/126 705/37 |
| 2015/0331908 A1* | 11/2015 | Duffy | ............... | G06F 16/2455 707/765 |
| 2016/0283563 A1* | 9/2016 | Hodjat | ............... | G06F 16/2465 |
| 2017/0323219 A1 | 11/2017 | Shahrzad et al. | .... | G06N 99/005 |

FOREIGN PATENT DOCUMENTS

| | | | |
|---|---|---|---|
| JP | H08-110804 | A | 4/1996 |
| JP | 2001325041 | A | 11/2001 |
| JP | 2003044665 | A | 2/2003 |
| JP | 2004240671 | A | 8/2004 |
| JP | 2004302741 | A | 10/2004 |
| JP | 2007207173 | A | 8/2007 |
| JP | 2007522547 | A | 8/2007 |
| WO | 2005073854 | A2 | 8/2005 |
| WO | 2010127039 | A1 | 11/2010 |
| WO | 2010127042 | A1 | 11/2010 |

OTHER PUBLICATIONS

Jeb et al., "A fast and elitist multiobjective genetic algorithm: NSGA-II," IEEE transactions on evolutionary computation, 6(2), 2002, pp. 182-197.

U.S. Appl. No. 13/358,381—Office Action dated Jul. 8, 2014, 30 pages.

Freitas, A., "A review of evolutionary algorithms for data mining." Soft Computing for Knowledge Discovery and Data Mining, Springer US, 2008, pp. 79-111.

U.S. Appl. No. 13/540,507—Office Action dated Sep. 9, 2014, 25 pages.

Bongard, J. C. et al., "Guarding Against Premature Convergence while Accelerating Evolutionary Search", GECCO'10: Proceedings of the 12th annual conference on Genetic and Evolutionary Computation, 8 pages (2010).

Hornby, Gregory S.; "The Age-Layered Population Structure (ALPS) Evolutionary Algorithm"; 2009; ACM; GECCO '09; 7 pages.

Gaspar-Cunha, A. et al., "A Multi-Objective Evolutionary Algorithm Using Neural Networks to Approximate Fitness Evaluations," Int'l J. Computers, Systems and Signals, 6(1) 2005. pp. 18-36.

Kosorukoff, A. "Using incremental evaluation and adaptive choice of operators in a genetic algorithm," Proc. Genetic and Evolutionary Computation Conference, GECCO- Sep. 2002, 7pp.

Nelson, A. "Fitness functions in evolutionary robotics: A survey and analysis," Robotics and Autonomous Systems 57 (Apr. 30, 2009) 345-370

Wu, A.S. et al., "An incremental fitness fitness function for partitioning parallel taks," Proc. Genetic and Evolutionary Computation Conf. (Aug. 2001) 8pp.

Whitehead, B.A. "Genetic Evolution of Radial Basis Function Coverage Using Orthogonal Niches," IEEE Transactions on Neural Networks, 7:6 (Nov. 1996) 1525-28.

Bui L.T. et al., "Local models: An approach to distributed multi-objective optimization," Computational Optimization and Applications, vol. 42, No. 1, Oct. 2007, pp. 105-139.

Castillo Tapia M.G. et al., "Applications of multi-objective evolutionary algorithms in economics and finance: A survey," Proc IEEE Congress on Evolutionary Computation, Sep. 2007, pp. 532-539.

Ducheyne, E. el al., "Is Fitness Inheritance Useful for Real-World Applications?" Evolutionary Multi-Criterion Optimization, ser. LNCS 2631, Spring 2003, pp. 31-42.

(56) References Cited

OTHER PUBLICATIONS

Enee, Gilles et al., "Classifier Systems Evolving Multi-Agent System with Distributed Elitism," Proc. 1999 Congress on Evolutionary Computation (CEC'99) vol. 3:6, Jul. 1999, pp. 1740-1746.
Gopalakrishnan, G. et al., "Optimal Sampling in a Noisy Genetic Algorithm for Risk-Based Remediation Design," Bridging the gap: meeting the world's water and environmental resources challenges, Proc. World Water Congress 2001, 8 pp.
Juille, H. "Evolution of Non-Deterministic Incremental Algorithms as a New Approach for Search in State Spaces," Proc. 6th Int'l Conf. on Genetic Algorithms, 1995, 8pp.
International Search Report dated Jul. 2, 2010 in PCT/US10/32847.
International Search Report dated Jun. 29, 2010 in PCT/US10/32841.
Sacks, J. et al. "Design and Anaiysis of Computer Experiments," Statistical Science 4:4, 1989, 409-435.
Torresen, J. "A Dynamic Fitness Function Applied to Improve the Generalisation when Evolving a Signal Processing Hardware Architecture," Proc EvoWorkshops 2002, 267-299 (12 pp).
Bartlett II, J.E. et al., "Organizational Research: Determining Appropriate Sample Size in Survey Research," IT, Learning, and Performance Journal 19(1) Spring 2001, 8pp.
Fitzpatrick, J.M. et al., "Genetic Algorithms in Noisy Environments," Machine Learning 3: 101-120, May 1988.
JP 2010-533295—Office Action, dated Apr. 16, 2013, 3 pp. (English translation).
León C. et al., "Parallel hypervolume-guided hyperheuristic for adapting the multi-objective evolutionary island model," Proc. 3rd Int'l Workshop on Nature Inspired Cooperative Strategies for Optimization Studies in Computational Intelligence, vol. 236, Nov. 2008, pp. 261-272.
López James A. et al., "MRMOGA: Parallel evolutionary multiobjective optimization using multiple resolutions," Proc. IEEE Congress on Evolutionary Computation, vol. 3, Sep. 2005, pp. 2294-2301.
Davarynejad, M. et al., "A Novel General Framework for Evolutionary Optimization: Adaptive Fuzzy Fitness Granulation," CEC Sep. 2007, 6pp.
Davarynejad, M. "Fuzzy Fitness Granulation in Evolutionary Algorithms for complex optimization," Master of Science Thesis, Ferdowsi Univ. of Mashhad, Jun. 2007, 30pp.
Salami, M. et al., "A fast evaluation strategy for evolutionary algorithms," Applied Soft Computing 2/3F (Jan. 2003) 156-173.
M.-R Akharzadeh-T. et al., "Friendship Modeling for Cooperative Co-Evolutionary Fuzzy Systems: A Hybrid GA-GP Algorithm," Proc. 22nd Int'l Conf. of N. American FIPS, Jul. 2003, pp. 61-66.
Mouret, J.B. et al., "Encouraging Behavioral Diversity in Evolutionary Robotics: An Empirical Study," MIT, Evolutionary Computation 20(1):91-133, 2012.
Myers, Raymond H. and Montgomery. Douglas C., Response Surface Methodology: Process and Product Optimization Using Designed Experiments, John Wiley and Sons, Inc., New York, 1995.
Poli R et al., "Genetic Programmig: An introductory Tutorial and a Survey of Techniques and Applications," Univ. Essex School of Computer Science and Eletronic Engineering Technical Report No. CES-475, Oct. 2007, 112 pp.
Georgilakis, P.S. "Genetic Algorithm Model for Profit Maximization of Generating Companies in Deregulated Electricity Markets," Applied Artificial Intelligence, Jul. 2009, 23:6,538-552.
Refaeilzadeh, P. et al., "Cross Validation" entry, Encyclopedia of Database Systems, eds. Özsu and Liu, Springer, 2009, 6pp.
Remde, S. et al. "Evolution of Fitness Functions to Improve Heuristic Performance," LION Dec. 8-10, 2007 II, LNCS 5313 pp. 206-219.
Sakauchi et al., Unifine: A Next Generation Financial Solution System of Nihon Unisys Ltd., Technology Review 'Unisys,' Japan, Nihon Unisys Ltd., Feb. 28, 2006, vol. 25, No. 4, pp. 14-15.
Schoreels C., "Agent based Genetic Algorithm Employing Financial Technical Analysis for Making Trading Decisions Using Historical Equity Market Data," IEEE/WIC/ACM International Conference on Intelligent Agent Technology (IAT2004), Beijing, China, Sep. 20-24, 2004, pp. 421-424.
Streichert F., "Introduction to Evolutionary Algorithms," paper to be presented Apr. 4, 2002 at the Frankfurt MathFinance Workshop Mar. 30, 2002, Frankfurt, Germany, XP55038571, 22 pp. (retrieved from the Internet: URL: http://www.ra.cs.uni-tuebingen.de/mita rb/streiche/publications/Introduction to E volutionary Algorithms.pdf).
Tanev, I. et al.. "Scalable architecture for parallel distributed implementation of genetic programming on network of workstations," J. Systems Architecture, vol. 47, Jul. 2001, pp. 557-572.
Laumanns, Marco et al.; "A Unified Model for Multi-Objective Evolutionary Algorithms with Elitism"; 2000; IEEE; pp. 46-53.
Ahn, Chang Wook et al.; "Elitism-Based Compact Genetic Algorithms"; 2003; IEEE; Transactions on Evolutionary Computation, vol. 7, No. 4; pp. 367-385.
Hornby, G.S., "ALPS: The Age-Layered Population Structure for Reducing the Problem of Premature Convergence," GECCO'06, Seattle, Jul. 2006, authored by an employee of the US Government, therefore in the public domain, 8pp.
Hornby, G.S., "A Steady-State Version of the Age-Layered Population Structure EA," Chapter 1 of Genetic Programming Theory and Practice VII, Riolo et al., editors, Springer 2009, 16pp.
Hornby, G.S., "Steady-State ALPS for Real-Valued Problems," GECCO'09, Montreal, Jul. 2009, Assoc. for Computing Machinery, 8pp.
idesign lab, "ALPS—The Age-Layered Population Structure," UC Santa Cruz web article printed Mar. 17, 2011 3 pp. (http://idesign.ucsc.edu/projects/alps.html).
Hodjat, B., et al., "Introducing an Age-Varying Fitness Estimation Function," Genetic Finance, Chapter 5, Genetic Programming Theory and Practice, Springer Science+Business Media New York, Copyright 2013, pp. 59-71.
Hodjat et. al., "nPool: Massively Distributed Simultaneous Evolution and Cross-Validation in EC-Star," Sentient Technologies, May 2015, pp. 1-12.
Al-Haj Baddar, "Finding Better Sorting Networks," Dissertation to Kent State University for PhD, May 2009, 86 pages.
Cuccu, G., et al., "When Novelty is Not Enough," vol. 6624 in Lecture Notes in Computer Science, published in Applications of Evolutionary Computation, Springer-Verlag Berlin Heidelberg, Copyright 2011, pp. 234-243.
Gomes et al., "Devising Effective Novelty Search Algorithms: A Comprehensive Empirical Study," GECCO '15, Madrid, Spain, Jul. 11-15, 2015, ACM (Copyright 2015), 8 pages.
Gomes et al., "Evolution of Swarm Robotics Systems with Novelty Search," published in Swarm Intelligence, vol. 7, Issue 2, ANTS Special Issue, 2013, pp. 115-144.
Gomes et al., "Progressive Minimal Criteria Novelty Search," Lisboa, Portugal, cited in Advances in Artificial Intelligence, Springer-Verlag Berlin Heidelberg, Copyright 2012, pp. 281-290.
Gupta et al., "An Overview of methods maintaining Diversity in Generic Algorithms," International Journal of Emerging Technology and Advanced Engineering, vol. 2, Issue 5, May 2012, pp. 56-60.
Hodjat et al, "Maintenance of a Long Running Distributed Genetic Programming System for Solving Problems Requiring Big Data," Genetic Finance Chap 1, published in Genetic Programming Theory and Practice XI as Chapter 4, 2014, 20 pages.
Kipfer et al., "UberFlow: A GPU-Based Particle Engine," Computer Graphics and Visualization, The Eurographics Association, Copyright 2004, 9 pages.
Krcah et al., "Combination of Novelty Search and Fitness-Based Search Applied to Robot Body-Brain Co-Evolution," Charles University, Prague Czech Republic, in Proceedings of the 13th Czech-Japan Seminar on Data Analysis and Decision Making in Service Science, 2010, 6 pages.
Lehman et al., "Abandoning Objectives: Evolution through the Search for Novelty Alone," Evolutionary Computation journal, (19):2, MIT Press, Copyright 2011, pp. 189-223.

(56) References Cited

OTHER PUBLICATIONS

Lehman et al., "Efficiently Evolving Programs through the Search for Novelty," Proceedings of the Genetic and Evolutionary Computation Conference, ACM, New York NY, Copyright 2010, 8 pages.

Lehman et al., "Evolving a Diversity of Creatures through Novelty Search and Local Competition," Proceedings of the Genetic and Evolutionary Computation Conference, ACM, New York, NY, 2011, 8 pages.

Lehman et al., "Extinction Events Can Accelerate Evolution," PLOS One, journal.pone.0132886, Aug. 12, 2015, 16 pages.

Lehman et al., "Overcoming Deception in Evolution of Cognitive Behaviors," University of Texas at Austin, ACM, Jul. 12-16, 2014, 8 pages.

Lehman et al., "Revising the Evolutionary Computation Abstraction: Minimal Criteria Novelty Search," Proceedings of the Genetic and Evolutionary ComputationConference, GECCO 2010, ACM, 2010, 8 pages.

OReilly, U., et al., "EC-Star: A Massive-Scale, HUB and Spoke, Distributed Genetic Programming System," Evolutionary Design and Optimization Group, published in Genetic Programming Theory and Practice X as Chapter 6, published in V as Chap 1, Springer New York, Copyright 2013, 13 pages.

Salge, C., et al., "Empowerment—An Introduction," published in Guided Self-Organization: Inception, Chap 4, University of Hertfordshire, Copyright 2013, pp. 67-114.

Secretan, J., et al., "Picbreeder: A Case Study in Collaborative Evolutionary Exploration of Design Space," Evolutionary Computation journal, MIT Press, Copyright 2011, 30 pages.

Shahrzad, H., et al., "Tackling the Boolean Multiplexer Function Using a Highly Distributed Genetic Programming System," published in Genetic Programming Theory and Practice XII, Springer International Publishing, Copyright 2015, pp. 167-179.

Valsalam, V.K., et al., "Using Symmetry and Evolutionary Search to Minimize Sorting Networks," Journal of Machine Learning Research 14, The University of Texas at Austin, Department of Computer Science, 2013, pp. 303-331.

Wissner-Gross, et al., "Causal Entropic Forces," Physical Review Letters, PRL 110, 168702, American Physical Society, Apr. 19, 2013, 5 pages.

U.S. Appl. No. 13/540,507—Notice of Allowance, dated Oct. 31, 2014, 9 pp.

U.S. Appl. No. 13/358,381—Notice of Allowance, dated Nov. 19, 2014, 5 pp.

U.S. Appl. No. 13/184,307—Office Action, dated Oct. 21, 2013, 16 pp.

U.S. Appl. No. 13/184,307—Notice of Allowance, dated Aug. 4, 2014, 9 pp.

U.S. Appl. No. 13/184,307—Office Action, dated Mar. 21, 2014, 36 pp.

U.S. Appl. No. 13/540,507—Response filed Oct. 15, 2014, 20 pp.

U.S. Appl. No. 13/358,381—Response dated Oct. 3, 2014, 20 pp.

U.S. Appl. No. 13/184,307—Response dated Jun. 23, 2014, 32 pp.

U.S. Appl. No. 13/184,307—Response dated Jan. 22, 2014, 19 pp.

U.S. Appl. No. 13/945,630—Office Action, dated Mar. 12, 2015, 18 pp.

U.S. Appl. No. 14/539,908—Notice of Allowance, dated Mar. 17, 2016, 5 pp.

U.S. Appl. No. 13/943,630—Notice of Allowance, dated May 19, 2016, 2 pp.

U.S. Appl. No. 13/943,630—Amendment After Allowance, dated Mar. 15, 2016, 16 pp.

U.S. Appl. No. 13/945,630—Amendment After Allowance, dated Dec. 9, 2015, 7 pp.

U.S. Appl. No. 13/943,630—Office Action, dated May 27, 2015, 42 pp.

U.S. Appl. No. 13/945,630—Office Action, dated Aug. 4, 2015, 22 pp.

U.S. Appl. No. 13/945,630—Response filed Jul. 13, 2015, 9 pp.

U.S. Appl. No. 13/358,381—Amendment After Allowance, filed Feb. 13, 2015, 20 pp.

U.S. Appl. No. 13/943,630—Response filed Sep. 23, 2015, 8 pp.

U.S. Appl. No. 14/539,908—Office Action, dated Oct. 1, 2015, 33 pp.

U.S. Appl. No. 13/945,630—Response filed Nov. 4, 2015, 12 pp.

U.S. Appl. No. 13/945,630—Notice of Allowance, dated Nov. 18, 2015, 8 pp.

U.S. Appl. No. 13/943,630—Notice of Allowance, dated Jan. 21, 2016, 28 pp.

U.S. Appl. No. 14/539,908—Response filed Feb. 1, 2016, 18 pp.

U.S. Appl. No. 14/595,991—Response filed Nov. 10, 2017, 29 pp.

U.S. Appl. No. 14/595,991—Office Action, dated Feb. 27, 2018, 19 pp.

U.S. Appl. No. 14/595,991—Response filed Jul. 27, 2018, 41 pp.

U.S. Appl. No. 14/595,991—Response filed May 22, 2018, 32 pp.

U.S. Appl. No. 14/595,991—Office Action, dated May 10, 2017, 32 pp.

Stanley, et al., "Why Greatness Cannot Be Planned: The Myth of the Objective," New York, NY, Springer (2015).

* cited by examiner

BEHAVIOR DOMINATED SEARCH IN EVOLUTIONARY SEARCH SYSTEMS

CROSS-REFERENCE TO OTHER APPLICATIONS

This application claims priority to U.S. Provisional Patent Application No. 62/467,061, entitled "DISCOVERING EVOLUTIONARY STEPPING STONES THROUGH BEHAVIOR DOMINATION," filed on 3 Mar. 2017, which is incorporated herein by reference.

The following U.S. patent applications are also incorporated by reference herein: U.S. Non-Provisional patent application Ser. No. 13/184,307 filed Jul. 15, 2011 and U.S. Non-Provisional patent application Ser. No. 14/595,991 filed Jan. 13, 2015.

FIELD OF THE TECHNOLOGY DISCLOSED

The technology disclosed relates generally to a computer system that performs evolutionary algorithms better. More particularly, the computer system uses a behavior-driven algorithm that is better able to find optimum solutions to a problem because it balances the use of fitness and novelty measures in evolutionary optimization.

BACKGROUND

In many environments, a large amount of data can be or has been collected which records experience over time within the environment. For example, a healthcare environment may record clinical data, diagnoses and treatment regimens for a large number of patients, as well as outcomes. A business environment may record customer information such as who they are and what they do, and their browsing and purchasing histories. A computer security environment may record a large number of software code examples that have been found to be malicious. Despite the large quantities of such data, or perhaps because of it, deriving useful knowledge from such data stores can be a daunting task.

The process of extracting patterns from such data sets is known as data mining. Many techniques have been applied to the problem, but the present discussion concerns a class of techniques known as genetic algorithms. Genetic algorithms have been applied to all of the above-mentioned environments.

Evolutionary algorithms, which are supersets of Genetic Algorithms, are good at traversing chaotic search spaces. According to Koza, J. R., "Genetic Programming: On the Programming of Computers by Means of Natural Selection," MIT Press (1992), incorporated by reference herein, an evolutionary algorithm can be used to evolve complete programs in declarative notation. The basic elements of an evolutionary algorithm are an environment, a model for a genotype (referred to herein as an "individual"), a fitness function, and a procreation function. An environment may be a model of any problem statement. An individual may be defined by a set of rules governing its behavior within the environment. A rule may be a list of conditions followed by an action to be performed in the environment. A fitness function may be defined by the degree to which an evolving rule set is successfully negotiating the environment. A fitness function is thus used for evaluating the fitness of each individual in the environment. A procreation function generates new individuals by mixing rules among the fittest parent individuals. In each generation, a new population of individuals is created.

At the start of the evolutionary process, individuals constituting the initial population are created randomly, by putting together the building blocks, or alphabets, that form an individual. In genetic programming, the alphabets are a set of conditions and actions making up rules governing the behavior of the individual within the environment. Once a population is established, it is evaluated using the fitness function. Individuals with the highest fitness are then used to create the next generation in a process called procreation. Through procreation, rules of parent individuals are mixed, and sometimes mutated (i.e., a random change is made in a rule) to create a new rule set. This new rule set is then assigned to a child individual that will be a member of the new generation. In some incarnations, known as elitist methods, the fittest members of the previous generation, called elitists, are also preserved into the next generation.

A common problem with evolutionary algorithms is that of premature convergence: after some number of evaluations the population converges to local optima and no further improvements are made no matter how much longer the algorithm is run. In one of a number of solutions to this problem, known as the Age-Layered Population Structure (ALPS), an individual's age is used to restrict competition and breeding between individuals in the population. In the parlance of ALPS, "age" is a measure of the number of times that an individual's genetic material has survived a generation (i.e., the number of times it has been preserved due to being selected into the elitist pool).

When using genetic algorithms to mine a large database, it may not be practical to test each individual against the entire database. The system therefore rarely if ever knows the true fitness of any individual. Rather, it knows only an estimate of the true fitness, based on the particular subset of data samples on which it has actually been tested. The fitness estimate itself, therefore, varies over time as the individual is tested on an increasing number of samples.

In a data mining environment with multiple solution landscapes, the evolutionary data mining system might generate some stepping stone individuals. Stepping stone individuals are individuals that do not necessarily have a high fitness estimate, but can have one or more critical parts of a future optimal individual. Despite their potential value, there is always a risk that before the stepping stone individual can be effectively utilized during procreation to create better individuals, they may get displaced by some other individuals that do not have the stepping stone individuals' critical parts but have marginally better fitness estimate. Considering only the fitness estimates of individuals during the evolution cannot ensure a diverse set of patterns or emergence of new patterns.

For example, in a healthcare embodiment, an individual diagnosing low blood pressure will have a lower fitness score than individuals diagnosing high blood pressure when tested on a subset of high blood pressure data samples. Therefore, if high blood pressure data samples are used for testing early in the testing process, there is a possibility that the competition module may prematurely discard the individual diagnosing low blood pressure from the candidate individual pool based on its low fitness score.

Novelty search has shown promise in evolutionary data mining system by collecting diverse stepping stones. Novelty search ranks individuals based on how different one individual is from other individuals. A novelty estimate of an individual is estimated in the space of behaviors, i.e., vectors containing semantic information about how an individual achieves its performance when it is evaluated. However, novelty search can become increasingly unfocused in an environment where a large number of possible behaviors can exist.

Therefore, a behavior-driven search is desired that promotes individual diversity without the search becoming unfocused in a large, complex data mining environment. It is in this kind of environment that embodiments of the present invention reside.

SUMMARY

Roughly described, a computer system uses a behavior-driven algorithm that is better able to find optimum solutions to a problem by balancing the use of fitness and novelty measures in evolutionary optimization. In competition among candidate individuals, a domination estimate between a pair of individuals is determined by both their fitness estimate difference and their behavior difference relative to one another. An increase in the fitness estimate difference of one individual of the pair over the other increases the domination estimate of the first individual. An increase in the behavior distance between the pair of individuals decreases the domination estimate of both of the individuals. Individuals with a higher domination estimate are more likely to survive competitions among the candidate individuals.

A computer-implemented evolutionary data mining system includes a memory storing a candidate individual database in which each candidate individual has a respective fitness estimate and a testing experience. The data mining system further includes a processing unit which tests individuals from the candidate individual pool on training data and updates the fitness estimate associated with the individuals in dependence upon the tests. Testing individuals from the pool of candidate individuals also includes identifying a behavioral value of the individual when tested against the portion of the training data, according to a predefined measure of behavior. An individual harvesting module provides for deployment selected ones of the individuals from the candidate individual pool. A competition module selects individuals for discarding from the candidate individual pool in dependence upon their domination estimate to achieve a diverse and optimal population of individuals. The competition module builds a retention set of N individuals to retain and discards from the pool all individuals in the pool that are not in the retention set.

The above summary of the invention is provided in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description that is presented later. Particular aspects of the invention are described in the claims, specification, and drawings.

BRIEF DESCRIPTION OF THE DRAWINGS

The invention will be described with respect to specific embodiments thereof, and reference will be made to the drawings, in which.

DETAILED DESCRIPTION

Figure 1:
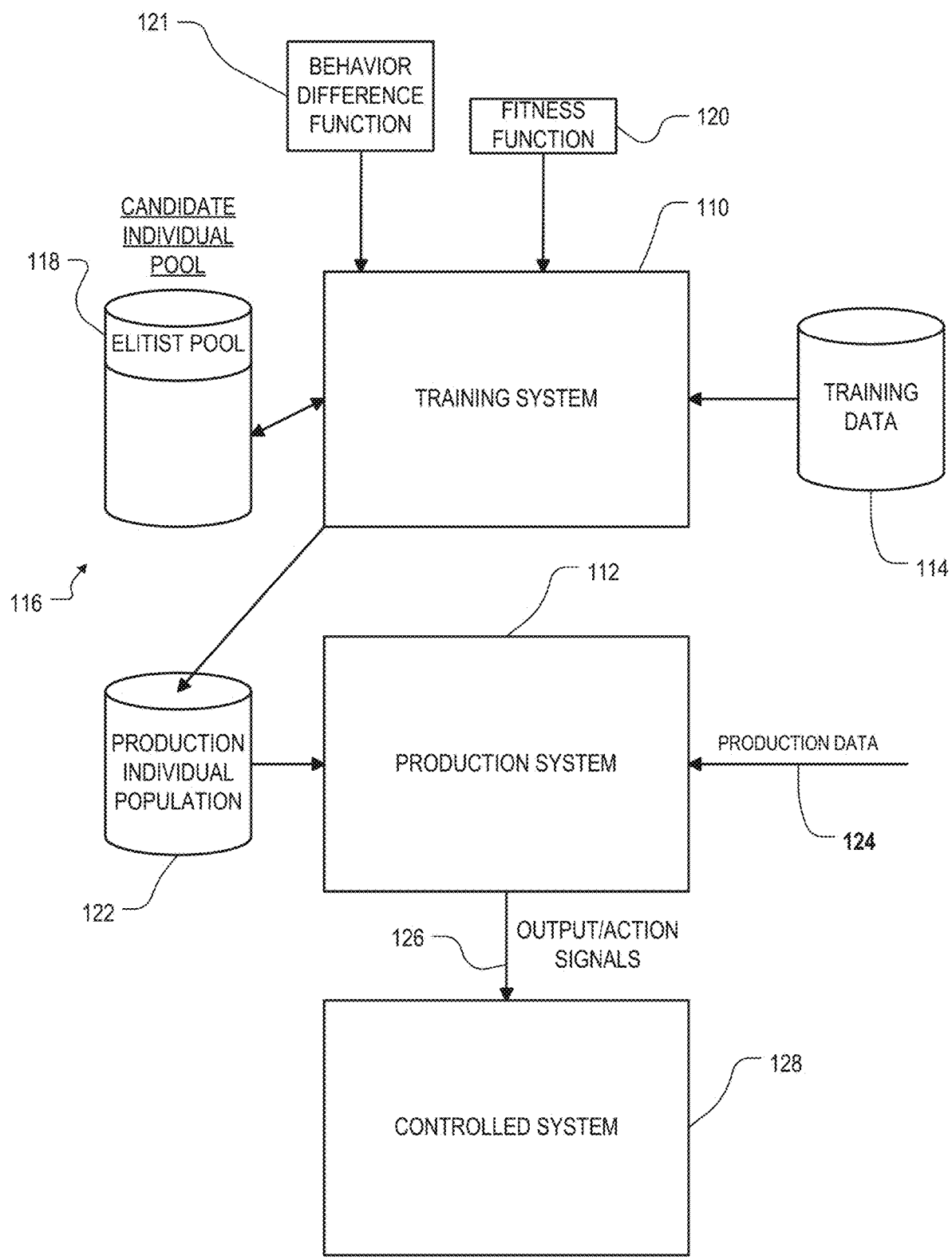
FIG. 1 is an overall diagram of an embodiment of a data mining system incorporating features of the invention.

The following description is presented to enable any person skilled in the art to make and use the invention and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

In the above-incorporated "DATA MINING TECHNIQUE WITH EXPERIENCE-LAYERED GENE POOL" application, a computer-implemented evolutionary data mining system includes a memory storing a candidate individual database in which each candidate individual has a respective fitness estimate; a candidate pool processor which tests individuals from the candidate individual pool on training data and updates the fitness estimate associated with the individuals in dependence upon the tests; and a candidate individual harvesting module providing for deployment selected ones of the individuals from the candidate individual pool, wherein the individual pool processor includes a competition module which selects individuals for discarding from the candidate individual pool in dependence upon both their updated fitness estimate and their testing experience level. An individual's experience is a measure of the number of times that the individual has been tested. Preferably the candidate individual database has an elitist pool containing multiple experience layers, where each experience layer comprises of individuals with a certain range of experience. The competition module causes individuals to compete only with other individuals in their same experience layer based on the individual's fitness scores.

In general, in embodiments herein, the elitist pool contains T experience layers numbered $L_1$-$L_T$, with T>1. The overall pool of candidate individuals also includes some that have not yet undergone sufficient numbers of tests to be considered for the elitist pool, and those individuals are considered herein to reside in a layer below the elitist pool, designed experience layer 0 ($L_0$). Each i'th one of the experience layers in [$L_0 \ldots L_{T-1}$] contains only individuals with a respective range of testing experience [ExpMin($L_i$) . . . ExpMax($L_i$)], each ExpMin($L_{i+1}$)>ExpMax($L_1$). The minimum experience level of the bottom experience layer $L_0$ is 0, and the top experience layer $L_T$ has a minimum experience level ExpMin($L_T$) but no maximum experience level. Preferably, the experience ranges of contiguous layers are themselves contiguous, so that ExpMin($L_{i+1}$)=ExpMax($L_i$)+1, for 0<=i<T. Note that testing experience level is a significantly different basis on which to stratify individuals in an elitist pool than age in the sense of Age-Layered Population Structure (ALPS).

In an embodiment, each layer i in the elitist pool (i.e., in layers [$L_1 \ldots L_T$]) is permitted to hold a respective maximum number of individuals, Quota($L_i$). The quota is chosen to be small enough to ensure competition among the individuals within the corresponding range of experience levels, but large enough to ensure sufficient diversity among the fit individuals that graduate to the next higher layer. Preferably the quota of each such layer is fixed, but in another embodiment, it could vary. The quota of layer $L_0$ is not chosen based on these criteria since the individuals in that layer do not yet compete. Preferably the number of layers T in the elitist pool is also fixed, but in another embodiment, it can vary.

As each individual gains more experience, assuming it is not displaced within its current experience layer, it will eventually graduate to the next higher experience layer. If the next higher experience layer is not yet full, then the individual may be added to that higher layer. If the higher layer is full, then the individual has to compete for its place in that layer. If the graduating individual does not successfully compete in the new layer, then the individual is discarded, and the individuals in the next higher layer will be retained. Otherwise, the graduating individual is accepted into the higher layer and a displaced individual. Note that the use of experience layers is only an embodiment; other embodiments are not required to use them, nor do they necessarily take experience into account at all in competition events.

In an embodiment, when individuals from the candidate individual pool are tested against a portion of the training data, a behavioral value of the individual is identified. As used herein, a "behavioral value" b(x) of an individual x in a data mining environment is a vector or a scalar number resulting from the evaluation of the individual in the data mining environment, according to a predefined measure of its behavior. For examples, for a robot navigating a maze, the predetermined measure of the robot's behavior of the robot may be a history of how the robot solves the task to get to its final destination, rather than the speed at which it reaches the final destination. In other words, the predetermined measure of behavior of an individual captures a space that is expected to have practical benefits.

As used herein, a "behavior difference" d(b(x),b(y)) between an individual x and an individual y is the distance between two individuals in an embedding space, as a function of their behavior.

As used herein, a "fitness estimate difference" between an individual x and an individual y is the difference in the fitness scores of the two individuals.

As used herein, a "domination estimate" between an individual x and an individual y is the relationship between the individuals x and y based on their fitness estimate difference and their behavior difference. The domination estimate between individuals x and y can be estimated by a function of the form:

$$\text{domination estimate}(x,y)=(f(x)-f(y))-w \cdot d(b(x),b(y)),$$

where f(x)–f(y) is the fitness estimate difference between individuals x and y, d(b(x),b(y)) is the behavior difference between individuals x and y, and w is a scaling parameter. Increasing the scaling parameter w increases the emphasis on novelty and diversity of individuals. Decreasing w increases the emphasis on fitness focused search. An increase in the fitness estimate difference between the pair of individuals x and y indicates that individual x from the pair of individuals performs better than individual y and therefore, the better performing individual x dominates individual y. On the other hand, an increase in the fitness estimate difference between the pair of individuals x and y increases individual x's domination estimate over individual y. An increase in the behavior difference between the pair of individuals x and y decreases their domination estimate as the increase in behavior difference indicates that individuals x and y differ in behavior and therefore, both might contain useful genetic information. That is, they might both perform equally well on training data seen so far, but because they operate in different ways, one might perform better than the other in future environments that might be encountered. Discarding individuals based on their domination estimate enables the data mining system to retain efficient stepping stone individuals. In one embodiment, when a pair of individuals are found where one of the individuals from the pair dominates over the other, the other individual can be discarded. Discarding individuals based on their domination estimates aims to formalize the idea that there is little value in retaining two individuals that behave similarly, and that as between the two of them the one to retain is the one that seems to be performing better so far.

Example Embodiment

FIG. 1 is an overall diagram of an embodiment of a data mining system incorporating features of the invention. The system is divided into three portions, a training system 110, a production system 112, and a controlled system 128. The training system 110 interacts with a database 114 containing training data, as well as with another database 116 containing the candidate individual pool. As used herein, the term "database" does not necessarily imply any unity of structure. For example, two or more separate databases, when considered together, still constitute a "database" as that term is used herein. The candidate individual pool database 116 includes a portion 118 containing the elitist pool. The training system 110 operates according to a fitness function 120, which indicates to the training system 110 how to measure the fitness of an individual and a behavior difference function 121, which indicates to the training system 110 how to measure the distance between the behaviors of two individuals. The training system 110 attempts to optimize for individuals that have the greatest fitness, however fitness is defined by the fitness function 120. The fitness function is specific to the environment and goals of the particular application. For example, the fitness function may be a function of the predictive value of the individual as assessed against the training data—the more often the individual correctly predicts the result represented in the training data, the more fit the individual is considered. In a financial asset trading environment, an individual might provide trading signals (e.g., buy, sell, hold current position, exit current position), and fitness may be measured by the individual's ability to make a profit, or the ability to do so while maintaining stability, or some other desired property. In the healthcare domain, an individual might propose a diagnosis based on patient prior treatment and current vital signs, and fitness may be measured by the accuracy of that diagnosis as represented in the training data.

The production system 112 operates according to a production individual population in another database 122. The production system 112 applies these individuals to production data 124, and produces outputs 126, which may be action signals or recommendations. In the financial asset trading environment, for example, the production data 124 may be a stream of real-time stock prices and the outputs 126 of the production system 112 may be the trading signals or instructions that one or more of the individuals in production individual population 122 outputs in response to the production data 124. In the healthcare domain, the production data 124 may be current, real-time or near-real-time patient data, and the outputs 126 of the production system 112 may be a suggested diagnosis or treatment regimen that one or more of the individuals in production individual population 122 outputs in response to the production data 124. The production individual population 122 is harvested from the training system 110 once or at intervals, depending on the embodiment. Preferably, only individuals from elitist pool 118 are permitted to be harvested. In an embodiment, further selection criteria can be applied in the harvesting process. Such further selection criteria may, for example, involve reference to the fitness trial histories of the individuals in the pool, and/or ancestry count.

The controlled system 128 is a system that is controlled automatically by the signals 126 from the production system. In the financial asset trading environment, for example, the controlled system may be a fully automated brokerage system which receives the trading signals via a computer network (not shown) and takes the indicated action. Depending on the application environment, the controlled system 128 may also include mechanical systems such as engines, air-conditioners, refrigerators, electric motors, robots, milling equipment, construction equipment, or a manufacturing plant.

While the embodiment of FIG. 1 operates the training system separately from the production system, aspects of the invention also apply to so-called "online" learning systems in which the training system and the production system are one. That is, training is performed on actual production data, and the outputs of the candidate individuals are actually used to operate the controlled system 128, even though the candidate individuals may not yet have been fully vetted. Candidate individuals are evaluated on actual feedback from the use of their outputs by the controlled system 128.

Figure 2:
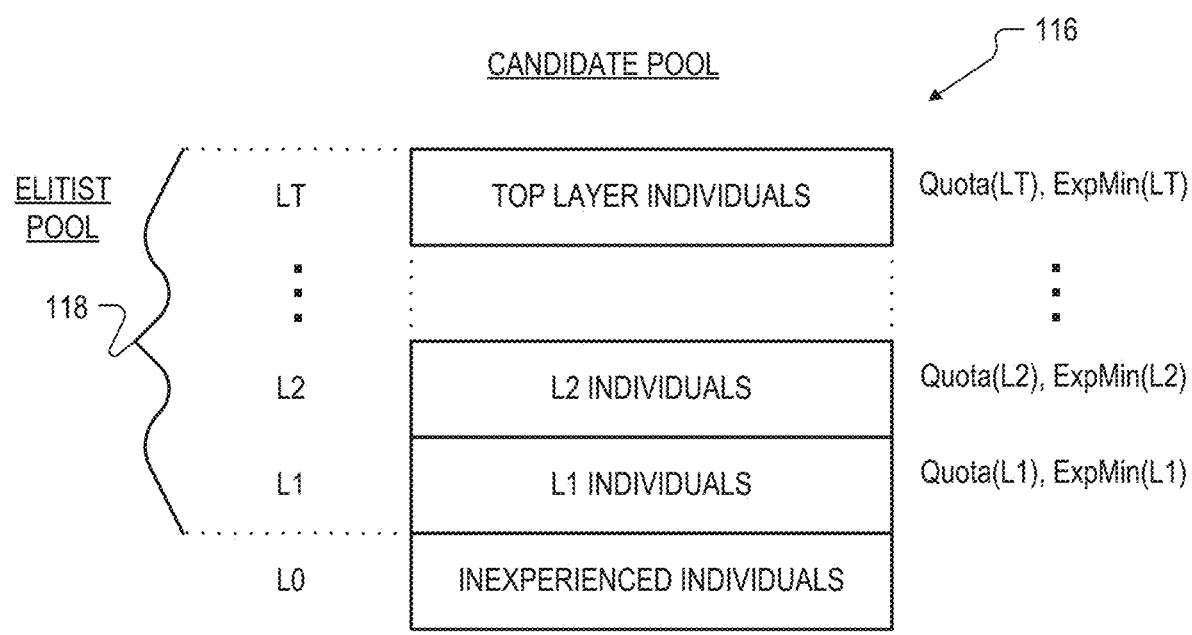
FIG. 2 is a symbolic drawing of the candidate individual pool in FIG. 1 according to an embodiment of the invention.

FIG. 2 is a symbolic drawing of the candidate pool 116 in FIG. 1. As can be seen, the individuals in the pool are stratified into T+1 "experience layers," labeled $L_0$ through $L_T$. The individuals in $L_0$ are very inexperienced (have been tested on only a relatively small number of samples in training data 114, if any), whereas the higher layers contain individuals in successively greater experience ranges. The layers $L_1$ through $L_T$ constitute the elitist pool 118 (FIG. 1). Each layer i in the elitist pool 118 has associated therewith three "layer parameters": a quota $Quota(L_i)$ for the layer, a range of experience levels $[ExpMin(L_i) \ldots ExpMax(L_i)]$ for the layer, and in some embodiments the minimum fitness $FitMin(L_i)$ for the layer. For example, an embodiment in the financial asset trading environment may have on the order of 40 or 50 layers in the elitist pool, each containing individuals with experience levels within a range on the order of 4000-5000 trials. The minimum experience level ExpMin ($L_1$) may be on the order of 8000-10,000 trials, and each layer may have a quota on the order of 100 individuals.

In the embodiment of FIG. 2, the quotas for all the layers in the elitist pool 118 are equal and fixed. In another embodiment, the quotas are not required to be fixed, nor are the quotas required to be the same across layers of the candidate pool. In addition, $ExpMin(L_0)=0$ in this embodiment. Also, as the experience ranges of the layers are contiguous, ExpMin of each layer can be inferred as one higher than ExpMax of the next lower layer, or ExpMax of each layer can be inferred as one lower than ExpMin of the next higher layer. Thus only the minimum experience level or the maximum experience level need be specified for each layer. In the embodiment, only the minimum experience levels are specified, and they are specified for layers $L_1$-$L_T$; in another embodiment, only the maximum experience levels are specified, and they are specified for layers $L_0$-$L_{T-1}$. In yet another embodiment, the size of the range of experience layers assigned to all the layers is constant, and only one minimum or maximum experience level is specified in the layer parameters; the remainder is calculated algorithmically as needed. Other variations will be apparent.

For an embodiment in which each layer is assigned a minimum fitness value, the FitMin( ) values associated with layers of the elitist pool are not specified a priori. Rather, they are filled by copying from the fitness estimate associated with the least fit individual in each layer. Whenever the fitness estimate of the least fit individual is updated, and whenever the least fit individual itself is replaced, the FitMin( ) value associated with the layer is updated correspondingly. The FitMin( ) values are needed for comparing to the fitness estimation of individuals coming up from the next lower layer, and having them associated directly with each layer can simplify this comparison. In another embodiment, each layer can instead contain a pointer to the least fit individual in the layer, and the comparison method can obtain the layer minimum fitness from that individual itself. In general, each layer has associated with it an "indication" of the minimum fitness in the layer. As used herein, an "indication" of an item of information does not necessarily require the direct specification of that item of information. Information can be "indicated" in a field by simply referring to the actual information through one or more layers of indirection, or by identifying one or more items of different information which are together sufficient to determine the actual item of information. In addition, the term "identification" and its variants are used herein to mean the same as "indication."

In one embodiment, the experience layers in candidate pool 116 define separate regions of memory, and the individuals having experience levels within the range of each particular layer are stored physically within that layer. Preferably, however, the experience layers are only implied by the layer parameters, and the individuals can actually be located anywhere in memory. In one embodiment, the individuals in candidate pool 116 are stored and managed by conventional database management systems (DBMS), and are accessed using SQL statements. Thus a conventional SQL query can be used to obtain, for example, the fitness estimate of the least fit individual in the highest layer. New individuals can be inserted into the candidate pool 116 using the SQL "insert" statement, and individuals being discarded can be deleted using the SQL "delete" statement. In another embodiment, the individuals in candidate pool 116 are stored in a linked list. In such an embodiment insertion of a new individual can be accomplished by writing its contents into an element in a free list, and then linking the element into the main linked list. Discarding of individuals involves unlinking them from the main linked list and re-linking them into the free list. Discarding causes an individual to be removed from competition, but in some embodiments, information about the individual may be recorded or logged for other purposes.

Figure 3:
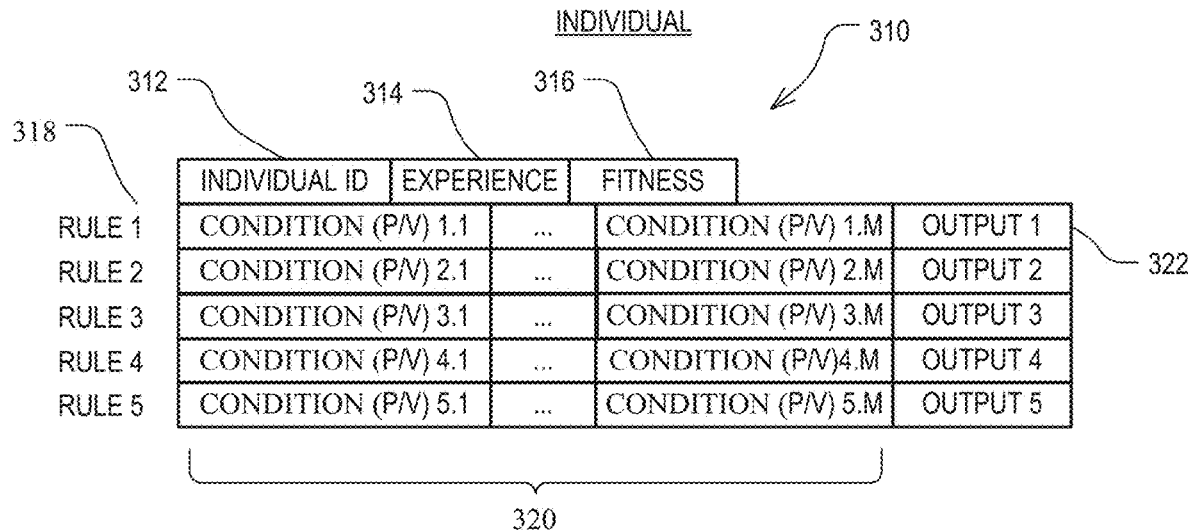
FIG. 3 is a symbolic drawing of an individual in either the candidate individual pool or the production individual population of FIG. 1, according to an embodiment of the invention.

FIG. 3 is a symbolic drawing of an individual 310 in either the candidate individual pool 116 or the production individual population 122. As used herein, an "individual" is defined by its contents. An individual created by procreation is considered herein to constitute a different individual than its parents, even though it retains some of its parents' genetic material. In this embodiment, the individual identifies an ID 312. Individuals in the candidate individual pool 116 include data items for a current fitness estimate 316, and an experience level 314, each data item of which is optional for individuals in the production individual population 122. In the embodiment of FIG. 3, individual 310 also includes one or more "rules" 318, each of which contains one or more conditions 320 and an output 322 to be asserted if all the conditions in a given sample are true. During procreation, any of the conditions or any of the outputs may be altered, or even entire rules may be replaced. The individual's experience level 314 increments by one for each sample of the training data 114 on which it is tested, and its overall fitness estimate 316 is determined by fitness function 120, averaged (or otherwise combined) over the all the trials.

Also as used herein, a "result" is the combination of outputs produced by an individual in response to a single data sample (either during training or in production), and the "performance" of an individual is a measure of how good the "result" was on that single sample. "Experience" level is a count of the number of samples on which the individual has been tested, though in systems that discard duplicate tests, it is a count of the number of unique samples on which the individual has been tested.

A rule is a conjunctive list of conditions in association with an output. In the embodiment of FIG. 3, the individual's conditions are all specified as parameter/value ("P/V") pairs. That is, if in the current sample, the specified parameter has the specified value (or range of values), then the condition is true. Another embodiment can also include conditions which are themselves conditioned on other items (such as other conditions in the rule or in a different rule or the result of another entire one of the rules). Yet another embodiment can also include conditions or rules which are specified procedurally rather than as P/V pairs. Many other variations will be apparent.

In a healthcare embodiment, an individual can be thought of as a set of rules predicting a patient's future state, given the patient's current and past states. In an embodiment, the set of rules may classify a patient's current state based on current and past states. The parameters on which the rules are based can be a patient's vital signs, and past treatment and medication history, for example. An example rule is as follows:

condition 1.1: pulse[t]>=120
condition 1.2: blood pressure[t−1]>=120
condition 1.3: blood pressure[t−6]<90

Output: high blood pressure related event
If condition 1.1 and condition 1.2 and condition 1.3, then Output.

The training data is arranged in the database 114 as a set of samples, each with parameters and their values, as well as sufficient information to determine a result that can be compared with an assertion made by an individual on the values in the sample. In one embodiment, the output is explicit, for example, a number set out explicitly in association with the sample. In such an embodiment, the fitness function can be dependent upon the number of samples for which the individual's output matches the result of the sample. In another embodiment, such as in the financial asset trading embodiment, the result may not be present in the test data itself, but rather derivable from the test data. For example, the sample may include the price of an asset at each tick throughout a trading day, and the training system 110 must hypothetically perform all the trading recommendations made by the individual throughout the trading day in order to determine whether and to what extent the individual made a profit or loss. The fitness function can be dependent upon the profit or loss that the individual, as a hypothetical trader, would have made using the tick data for the sample. Note that whereas in the embodiment of FIG. 3 the individuals are expressed in terms of rules, that is not required in all embodiments. In another embodiment, an individual might for example be expressed in terms of a vector of floating point numbers. Many other embodiments will be apparent to the skilled reader. In general, as used herein, individuals merely identify a potential solution to the problem provided to the system for solving.

Figure 4:
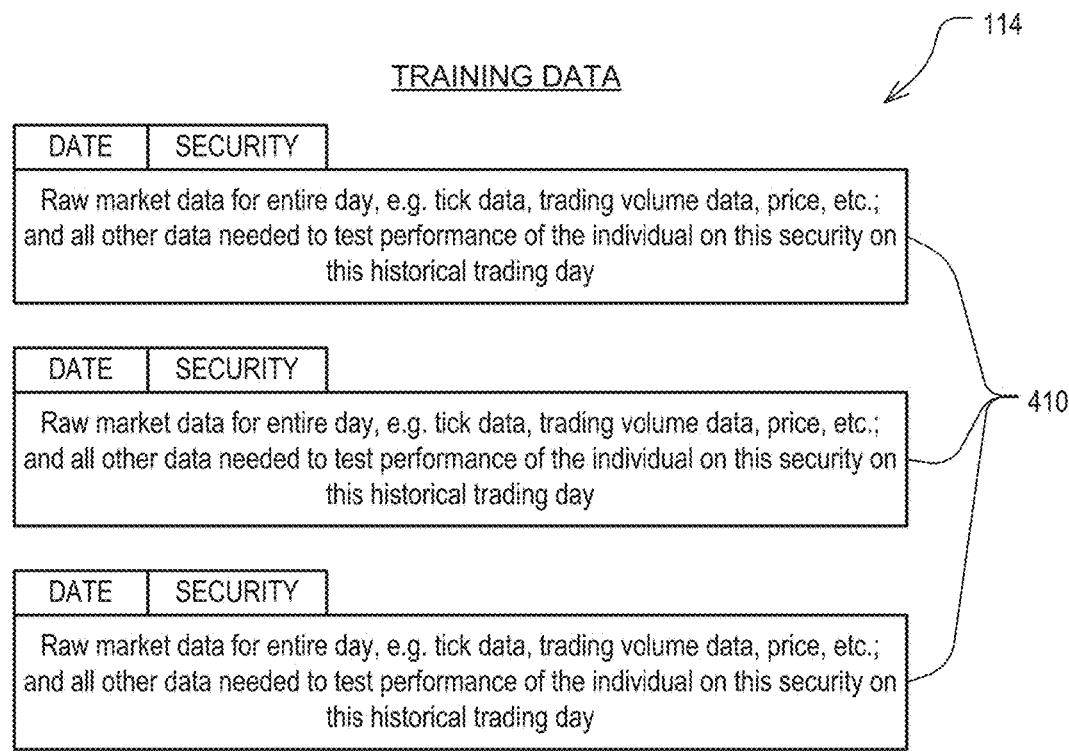
FIG. 4 is a symbolic drawing indicating how the training data database is organized, according to an embodiment of the invention.
Figure 5:
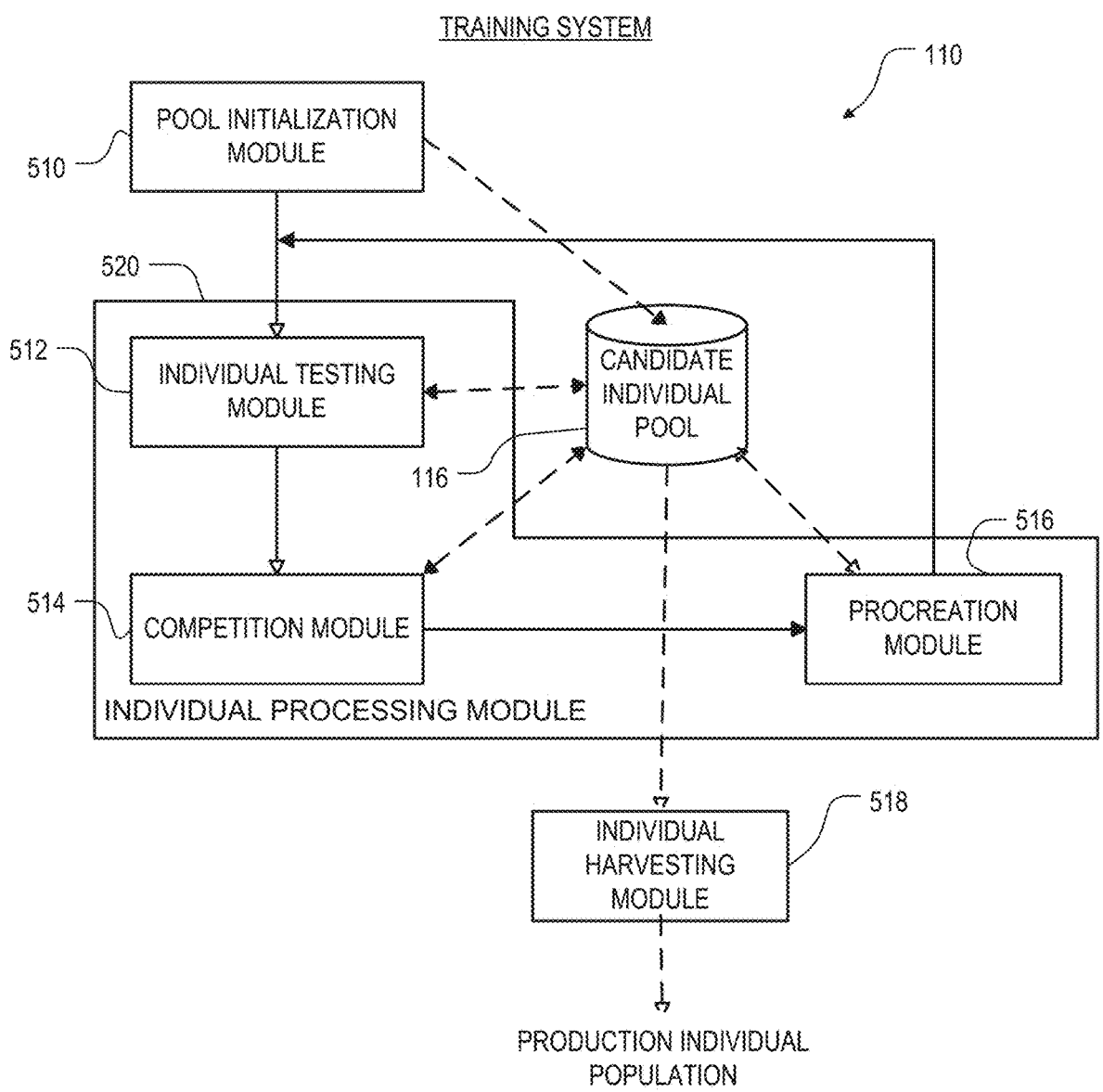
FIG. 5 illustrates modules that can be used to implement the functionality of the training system in FIG. 1, according to an embodiment of the invention.

FIG. 4 is a symbolic drawing indicating how the training data is organized in the database 114. The illustration in FIG. 4 is for the financial asset trading embodiment, and it will be understood how it can be modified for use in other environments. Referring to FIG. 4, three samples 410 are shown. Each sample includes a historical date, an identification of a particular security or other financial asset (such as a particular stock symbol), and raw historical market data for that financial asset on that entire trading day, e.g. tick data, trading volume data, price, etc.; and all other data needed to test performance of the individual's trading recommendations on this asset on this historical trading day. For example, the three samples of training data 410 could represent three days of stock tick data, each sample representing one day of the same security. Alternatively, the three samples could represent one day of stock tick data for each of three distinct securities. Any combination thereof may be used. Training System FIG. 5 illustrates various modules that can be used to implement the functionality of training system 110 (FIG. 1). Candidate individual pool 116 is also shown in the drawing. Solid lines indicate process flow, and broken lines indicate data flow. The modules can be implemented in hardware or software, and need not be divided up in precisely the same blocks as shown in FIG. 5. Some can also be implemented on different processors or computers or spread among a number of different processors or computers. In addition, it will be appreciated that some of the modules can be combined, operated in parallel or in a different sequence than that shown in FIG. 5 without affecting the functions achieved. Also as used herein, the term "module" can include "sub-modules," which themselves can be considered herein to constitute modules. In particular, the individual testing module 512, competition module 514, and procreation module 516 are also considered herein to be sub-modules of an individual pool processor module 520. The blocks in FIG. 5 designated as modules can also be thought of as flowchart steps in a method.

Referring to FIG. 5, the candidate individual pool 116 is initialized by pool initialization module 510, which creates an initial set of candidate individuals in $L_0$ of the individual pool 116. These individuals can be created randomly, or in some embodiments, a priori knowledge is used to seed the first generation. At the start, all individuals are initialized with an experience level of zero and a fitness estimate that is undefined.

Individual testing module 512 then proceeds to test the population in the individual pool 116 on the training data 114. Only a subset of the population in the individual pool 116 is tested at this point. As used herein, the term "subset," unless otherwise qualified, includes both proper and improper subsets as well as the null set. However, for the reasons explained above, the subset which is tested at this point is a non-null subset which includes only those individuals that have not yet reached the top layer $L_T$ of the elitist pool 118 (of which there are none initially). Each individual in the subset undergoes a battery of tests or trials on the training data 114, each trial testing the individual on one sample 410. In one embodiment, each battery might consist of only a single trial. Preferably, however, a battery of tests is much larger, for example on the order of 1000 trials. In one embodiment, at least the initial battery of tests includes at least ExpMin($L_1$) trials for each individual, to enable the initial individuals to qualify for consideration for the first layer of the elitist pool 118. Note there is no requirement that all individuals undergo the same number of trials. Note also that in an online learning embodiment, "testing" of an individual may involve using the individual to control the controlled system 128, and receiving any resulting feedback.

After the tests, individual testing module 512 updates the fitness estimate associated with each of the individuals tested. In an embodiment, the fitness estimate may be an average of the results of all trials of the individual. In this case, the "fitness estimate" can conveniently be indicated by two numbers: the sum of the performance measures of all trials of the individual, and the total number of trials that the individual has experienced. The latter number may already be maintained as the experience level of the individual. The fitness estimate at any particular time can then be calculated as follows:

$$\text{fitness estimate} = \frac{\sum_{i=1}^{n} \text{performance measure}_i}{n},$$

where performance measure$_i$ is the individual's performance measure when tested on data sample i, and n is the number of data samples on which the individual has been tested, given by the individual's experience level. In an embodiment such as this, "updating" of the fitness estimate can involve merely adding the performance measures from the most recent trials to the prior sum.

In another embodiment, the fitness estimate is capped at a certain level. In other words, for positive values of non-weightedFitness:

fitness estimate=Min(CAP_VALUE,non-weightedFitness).

This technique, which applies a form of weighting which is piecewise rather than smooth, has the effect of reducing the system's sensitivity to very large outlier values. In an online learning embodiment, the fitness of an individual depends on the positive or negative feedback received from use of the individual's outputs in production.

Once the fitness estimate and experience level are updated in the candidate individual pool for each tested individual, the competition module 514 performs competition among individuals, moves some individuals between experience layers, and may discard other individuals. More detail about the competition process is provided below. After the candidate individual pool 116 has been updated, a procreation module 516 selects a random subset of individuals from which to evolve new individuals. Only individuals in the elitist pool may be selected to procreate. Any conventional or future-developed technique can be used for procreation. In an embodiment, conditions, outputs, or rules from parent individuals are combined in various ways to form child individuals, and then, occasionally, they are mutated. The combination process, for example, may include crossover—i.e., exchanging conditions, outputs, or entire rules between parent individuals to form child individuals. New individuals created through procreation begin with an experience level of zero and with a fitness estimate that is undefined. These individuals are placed in $L_0$ of the individual pool 116. Preferably, after new individuals are created by combination and/or mutation, the parent individuals are retained. In this case, the parent individuals also retain their experience level and fitness estimates, and remain in their then-current elitist pool layers. In another embodiment, the parent individuals are discarded.

After procreation, individual testing module 512 operates again on the updated individual pool 116. The process continues repeatedly.

Sometime after the top layer of elitist pool 118 is full, individuals can be harvested for use by production system 112. Individual harvesting module 518 retrieves individuals for that purpose. In one embodiment, individual harvesting module 518 retrieves individuals periodically, whereas in another embodiment it retrieves individuals only in response to user input. Individual harvesting module 518 selects only from the top layer $L_T$, and can apply further selection criteria as well in order to choose desirable individuals. For example, in one embodiment it selects only the fittest individuals from $L_T$. The individuals may also undergo further validation as part of this further selection process, by testing on historical data not part of training data 114. The individuals selected by the individual harvesting module 518 are written to the production individual population database for use by production system 112 as previously described. In an online learning embodiment, there may be no separate harvesting module since the candidate individuals essentially are already in production.

As mentioned above, competition module 514 manages the graduation of individuals from lower experience layers in the candidate individual pool 116 to higher experience layers. This process can be thought of as occurring one individual at a time, as follows. First, a loop is begun through all individuals whose experience level has changed since the last time competition module 514 was executed. If the current individual's experience level has not increased sufficiently to qualify it for the next experience layer in the elitist pool 118, then the individual is ignored, and the next one is considered. If the current individual's experience level has increased sufficiently to qualify it for a new experience layer, then the competition module 514 determines whether the target experience layer is already at quota. If not, then the individual is simply moved into t the target experience level. If the target experience layer is full, then the competition module 514 adds the current individual to the target experience layer and discards at least one individual in the target experience layer on dependence upon the dominance estimate of the individuals in the target experience layer. The process then moves on to consider the next individual in sequence. Note that while individuals typically move up by only one experience layer at a time, that is not a requirement in all embodiments. In some embodiments, such as in a client/server embodiment, it may happen that a particular individual is not considered for advancement within the elitist pool 118 until after its experience level has increased sufficiently for it to jump past one or more experienced layers.

In an embodiment that enforces an elitist pool minimum fitness, the step in which the fitness estimate of the current individual is compared to the minimum fitness of the target experience layer can further include a test of whether the current individual's fitness estimate satisfies the elitist pool minimum fitness. Typically this latter test is applied only to individuals graduating out of level 0, but as mentioned previously, could be applied to individuals being considered for other layers in the elitist pool 118 as well. If the current individual does not satisfy the elitist pool minimum fitness, then it is discarded.

The above routine processes individuals sequentially, and different embodiments can implement different sequences for processing the individuals. Note that the processing sequence can affect the results if, for example, an individual in layer $L_i$ is being considered for layer $L_{i+1}$ at the same time that an individual in layer $L_{i-1}$ is being considered for layer $L_i$. If the former test occurs first, then a hole will be opened in layer $L_i$ and the individual graduating from layer $L_{i-1}$ will be promoted into layer $L_i$ automatically. If the latter test occurs first, then the individual graduating from layer $L_{i-1}$ will have to compete for its place in layer $L_i$ (assuming layer $L_i$ is at quota). In another embodiment, individuals are considered layer by layer either according to their target layer after promotion, or according to their current layer prior to promotion. Again, the sequence of individuals to consider within each layer will depend on the embodiment, as will the sequence in which the layers themselves are considered.

Figure 6:
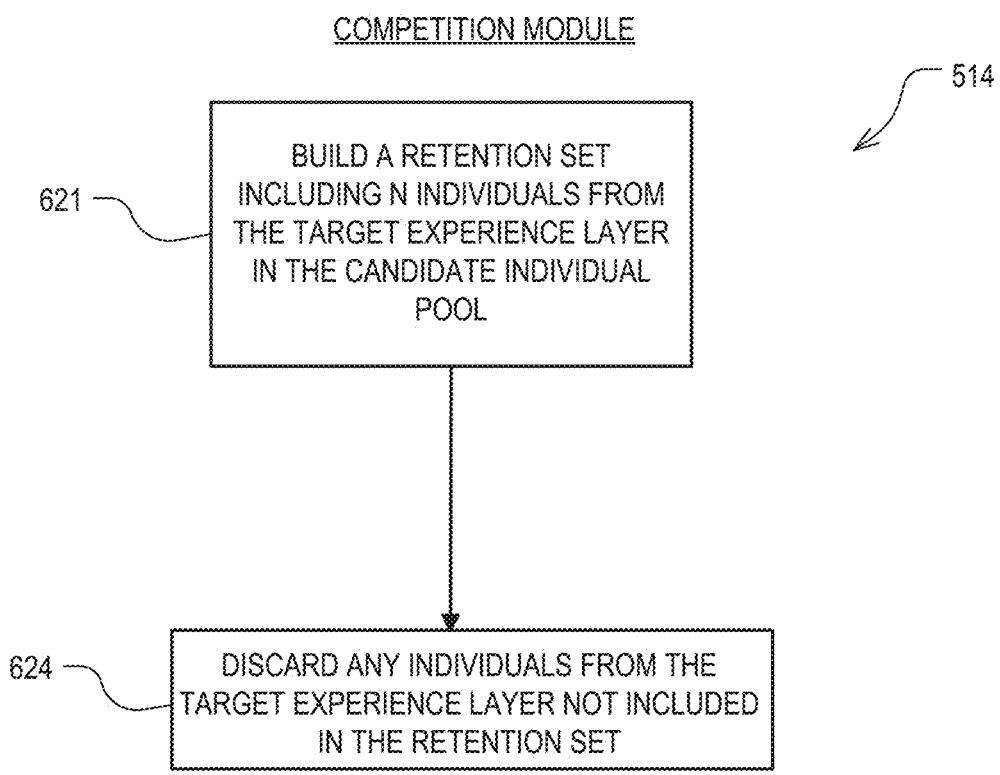
FIG. 6 illustrates a method of operation of the competition module in FIG. 5, according to an embodiment of the invention.

FIG. 6 illustrates a bulk-oriented method of operation of competition module 514. In the embodiment of FIG. 6, individuals have graduated from lower experience layers to a target experience layer. Addition of the new individuals exceeds the target experience layer Quota($L_{target}$) of N individuals. Therefore, one or more individuals in the target experience layer need to be discarded to maintain N individuals in the target experience layer. The competition module 514 selects individuals for discarding from the target experience layer in dependence upon their domination estimate. These executions of competition module 514 are sometimes referred to herein as competition "events," and each comparison made between the dominance estimate of one individual and that of another is sometimes referred to herein as a comparison "instance."

In step 621, the competition module 514 builds a retention set of N individuals, N being the Quota($L_{target}$). In step 624, the competition module 514 discards from the target experience layer all individuals in the pool that are not in the retention set. Therefore, after discarding, the target experience layer contains the N individuals from the retention set.

Figure 7A:
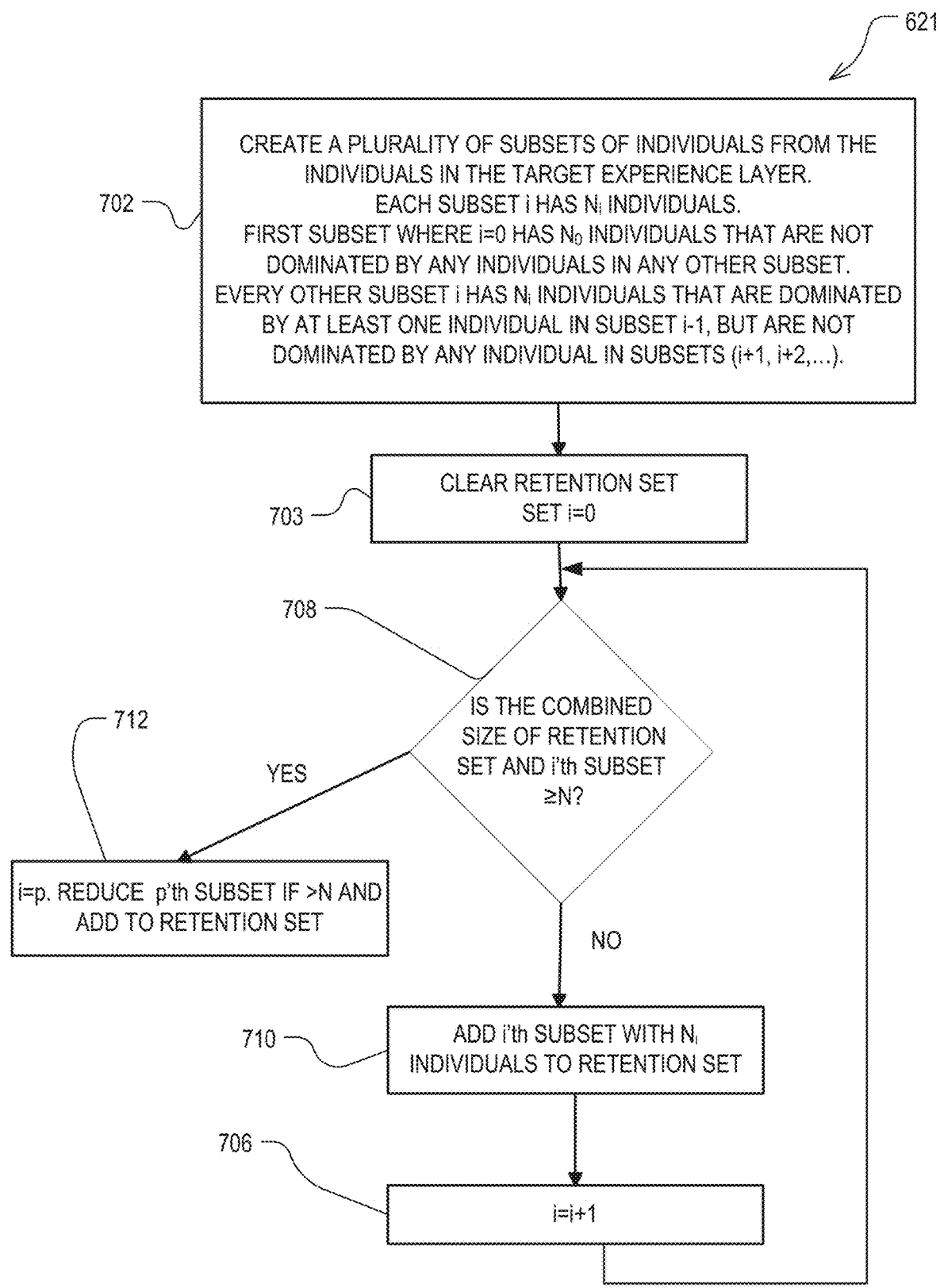
FIG. 7 (FIGS. 7A and 7B collectively) illustrates a method of building a retention set by the competition module in FIG. 5, according to an embodiment of the invention.

FIG. 7A illustrates a method by which the computer system can build a retention set, according to an embodiment of the invention. A retention set is built by creating a plurality of subsets of individuals from the individuals in the target experience layer at step 702. Each subset i has includes $N_i$ individuals. The first subset where i=0 has $N_0$ individuals that are not dominated by any individuals in any other subset. Whether one individual is dominated by another is determined by estimating the dominance estimate between the two individuals. Every other subset i in the plurality of subsets, i>0, has $N_i$ individuals that are dominated by individuals in subset i−1 but are not dominated by any individual in any higher order subset (i+1, i+2, . . . ).

At step 703, the retention set is cleared and i is set to 0.

At step 704, the first subset with i=0 is added to the retention set. The first subset includes $N_0$ individuals that are not dominated by any other individuals in the target experience layer. In step 708, the competition module 514 first checks whether the combined size of the i'th subset and the retention set is greater than or equal to the N, the quota of the target experience layer. If the combined size is less than N, the entire i'th subset is added to the retention set (step 710). The value of i is incremented by 1 (step 708), and the i+1'th subset is considered for adding to the retention set. If in step 708, the combined size of the retention set and the i'th subset will be greater than or equal to N, then the current subset (now called subset p) will be the last one to be added to the retention set in step 712. But since the combined size might now exceed the quota N of the retention set, step 712 first "reduces" the number of individuals in the p'th subset before adding them to the retention set. The reduction reduces the number of individuals in the p'th subset such that combined size of the p'th subset and the retention set is equal to the N.

Figure 7B:
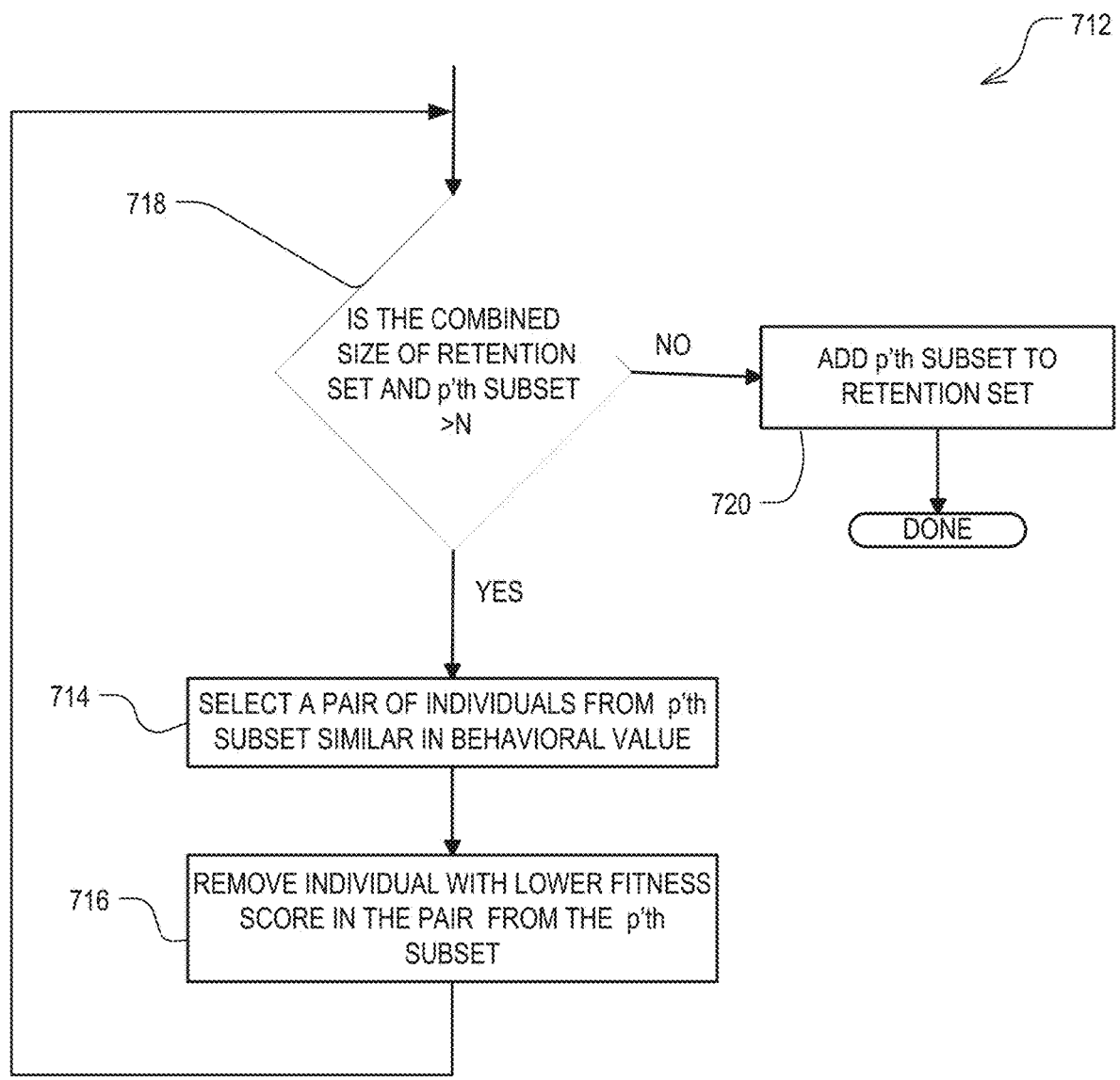

FIG. 7B illustrates a method by which the computer system can reduce the p'th subset before being added to the retention set. At step 718, it is first determined whether the combined size of the retention set and the p'th subset will exceed N. If not, then no reduction is needed. The p'th subset is added in its entirety to the retention set in step 720 and the procedure completes. If the combined size of the retention set and the p'th subset will exceed N, then at step 714, two individuals are selected from the p'th subset that have the smallest behavior difference. At step 716, the individual with the lower fitness estimate between the two individuals selected in step 714 is discarded from the p'th subset. The procedure then returns to step 718, where it is again determined whether the combined size of the retention set and the now-reduced p'th set is still greater than N. If not, then the reduction is complete and the entire remaining p'th subset is added to the retention set in step 720. If further reduction is needed, then another pair of individuals with the smallest behavior difference is selected (step 714), and the one with the lower fitness is discarded (step 716). The reduction process continues, discarding individuals from the p'th subset until the combined size of the retention set and the reduced p'th set is N. When the combined size of the retention set and the reduced p'th set is N, the p'th subset is added to the retention set (step 720). It can be seen that the combined procedures of FIGS. 7A and 7B adds to the retention set individuals that are dominated by individuals in the retention set but not by any other individuals in the pool, until the number of individuals in the retention set reaches N.

Computer Hardware

Figure 8:
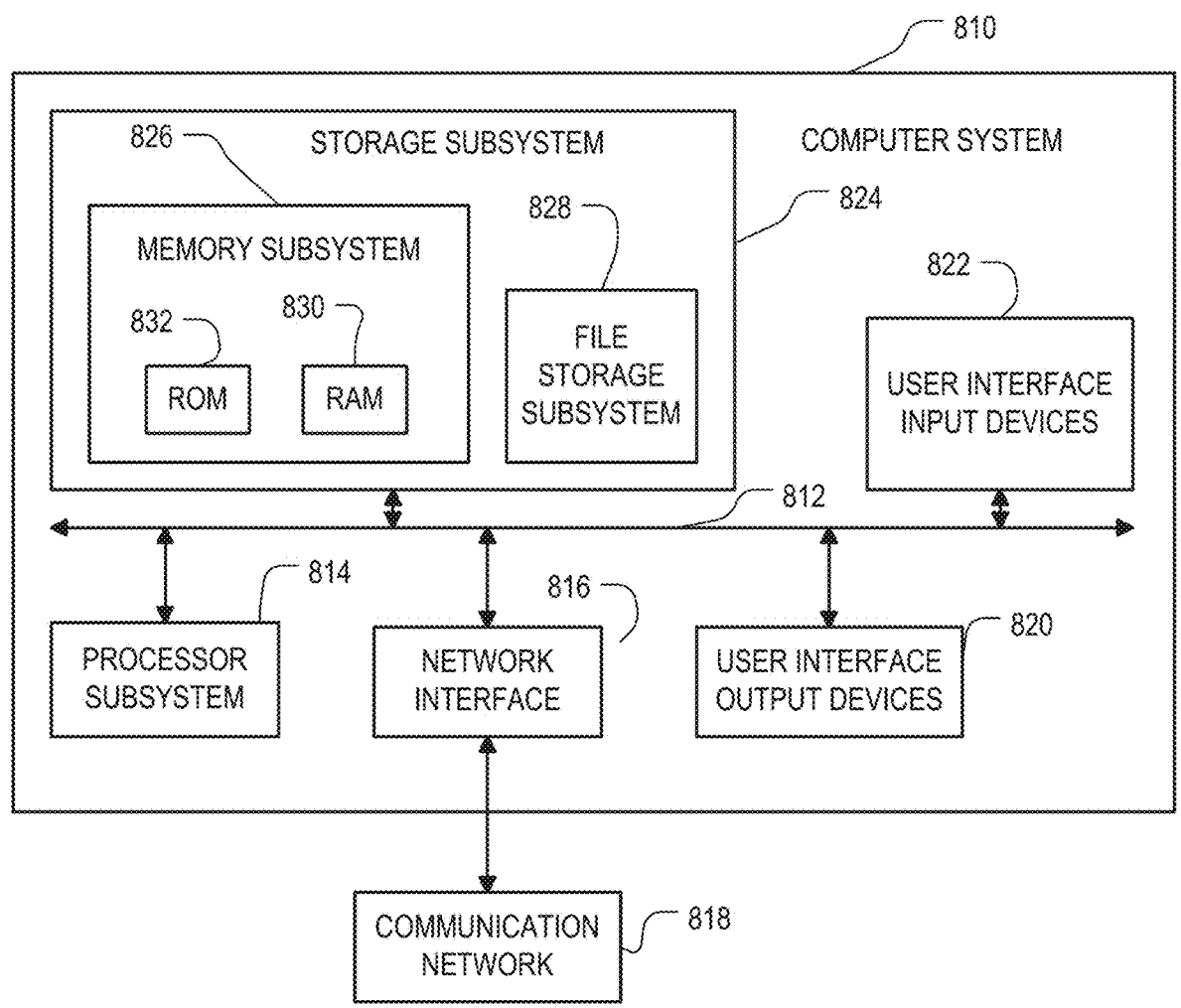
FIG. 8 is a simplified block diagram of a computer system that can be used to implement either or both of the training system or production system in FIG. 1, and/or the training server and clients in FIG. 9, according to an embodiment of the invention.

FIG. 8 is a simplified block diagram of a computer system 810 that can be used to implement training system 110, production system 126, or both. While FIGS. 1, 5, 6, 7, 9, 10 and 11 indicate individual components for carrying out specified operations, it will be appreciated that each component actually causes a computer system such as 810 to operate in the specified manner.

Computer system 810 typically includes a processor subsystem 814 which communicates with a number of peripheral devices via bus subsystem 812. These peripheral devices may include a storage subsystem 824, comprising a memory subsystem 826 and a file storage subsystem 828, user interface input devices 822, user interface output devices 820, and a network interface subsystem 816. The input and output devices allow user interaction with computer system 810. Network interface subsystem 816 provides an interface to outside networks, including an interface to communication network 818, and is coupled via communication network 818 to corresponding interface devices in other computer systems. Communication network 818 may comprise many interconnected computer systems and communication links. These communication links may be wireline links, optical links, wireless links, or any other mechanisms for communication of information. While in one embodiment, communication network 818 is the Internet, in other embodiments, communication network 818 may be any suitable computer network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 822 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 810 or onto computer network 818.

User interface output devices 820 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 810 to the user or to another machine or computer system. In particular, an output device of the computer system 810 on which production system 112 is implemented, may include a visual output informing a user of action recommendations made by the system, or may include a communication device for communicating action signals directly to the controlled system 128. Additionally or alternatively, the communication network 818 may communicate action signals to the controlled system 128. In the financial asset trading environment, for example, the communication network 818 transmits trading signals to a computer system in a brokerage house which attempts to execute the indicated trades.

Storage subsystem 824 stores the basic programming and data constructs that provide the functionality of certain embodiments of the present invention. For example, the various modules implementing the functionality of certain embodiments of the invention may be stored in storage subsystem 824. These software modules are generally executed by processor subsystem 814. Storage subsystem 824 also stores the candidate individual pool 116, the training database 114, and/or the production individual population 122. Alternatively, one or more of such databases can be physically located elsewhere, and made accessible to the computer system 810 via the communication network 818.

Memory subsystem 826 typically includes a number of memories including a main random access memory (RAM) 830 for storage of instructions and data during program execution and a read only memory (ROM) 832 in which fixed instructions are stored. File storage subsystem 828 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 828. The host memory 826 contains, among other things, computer instructions which, when executed by the processor subsystem 814, cause the computer system to operate or perform functions as described herein. As used herein, processes and software that are said to run in or on "the host" or "the computer", execute on the processor subsystem 814 in response to computer instructions and data in the host memory subsystem 826 including any other local or remote storage for such instructions and data.

Bus subsystem 812 provides a mechanism for letting the various components and subsystems of computer system 810 communicate with each other as intended. Although bus subsystem 812 is shown schematically as a single bus, alternative embodiments of the bus subsystem may use multiple busses.

Computer system 810 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 810 depicted in FIG. 8 is intended only as a specific example for purposes of illustrating the preferred embodiments of the present invention. Many other configurations of computer system 810 are possible having more or less components than the computer system depicted in FIG. 8.

Client/Server Embodiment

In some environments, the training data used to evaluate an individual's fitness can be voluminous. Therefore, even with modern high processing power and large memory capacity computers, achieving quality results within a reasonable time is often not feasible on a single machine. A large individual pool also requires a large memory and high processing power. In one embodiment, therefore, a client/server model is used to provide scaling in order to achieve high quality evaluation results within a reasonable time period. Scaling is carried out in two dimensions, namely in pool size as well as in evaluation of the same individual to generate a more diverse individual pool so as to increase the probability of finding fitter individuals. In the client/server embodiment, the individual pool is distributed over a multitude of clients for evaluation. Each client maintains its own client-centric individual pool using data from training database 114, which it may receive in bulk or periodically on a sustained and continuing basis. Individuals that satisfy one or more predefined conditions on a client computer are transmitted to the server to form part of a server-centric individual pool.

Distributed processing of individuals also may be used to increase the speed of evaluation of a given individual. To achieve this, individuals that are received by the server but have not yet been tested on a certain number of samples, or have not yet met one or more predefined conditions, may be sent back from the server to a multitude of clients for further evaluation. The evaluation result achieved by the clients (alternatively called herein a partial evaluation) for an individual is transferred back to the server. The server merges the partial evaluation results of an individual with that individual's fitness estimate at the time it was sent to the clients to arrive at an updated fitness estimate for that individual in the server-centric individual pool. For example, assume that an individual has been tested on 500 samples and is sent from the server to, for example, two clients each instructed to test the individual on 100 additional samples. Accordingly, each client further tests the individual on the additional 100 samples and reports its own client-centric fitness estimate to the server. The server combines these two estimates with the individual's fitness estimate at the time it was sent to the two clients to calculate an updated server-centric fitness estimate for the individual. The combined results represent the individual's fitness evaluated over 700 days. In other words, the distributed system, in accordance with this example, increases the experience level of an individual from 500 samples to 700 samples using only 100 different training samples at each client. A distributed system, in accordance with the present invention, is thus highly scalable in evaluating its individuals.

Advantageously, clients are enabled to perform individual procreation locally, thereby improving the quality of their individuals. Each client is a self-contained evolution device, not only evaluating the individuals in its own pool, but also creating a new generation of individuals and moving the evolutionary process forward locally. Thus clients maintain their own client-centric individual pool which need not match each other's or the server-centric individual pool. Since the clients continue to advance with their own local evolutionary process, their processing power is not wasted even if they are not in constant communication with the server. Once communication is reestablished with the server, clients can send in their fittest individuals to the server and receive additional individuals from the server for further testing.

Figure 9:
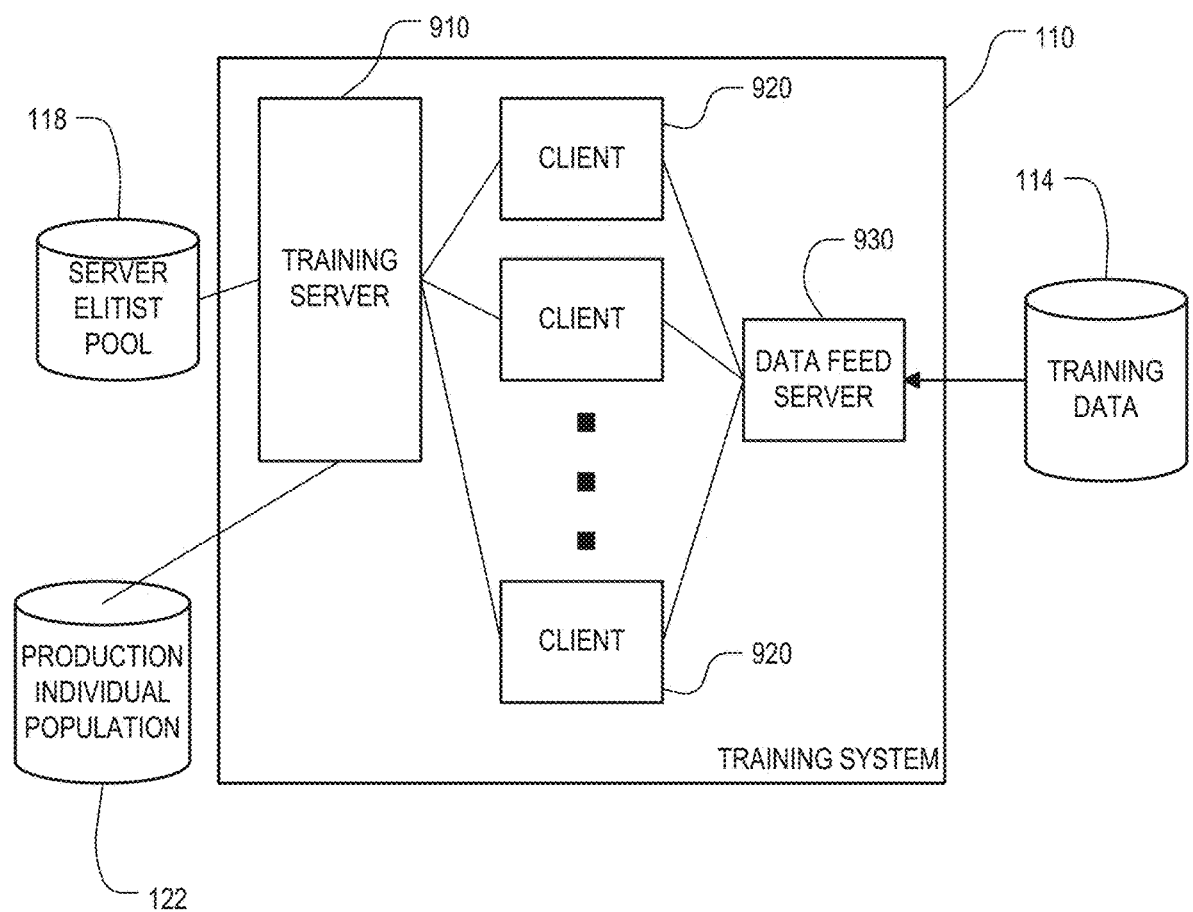
FIG. 9 is a high-level block diagram of an example embodiment of the training system of FIG. 1 using a network computing system.

FIG. 9 is a high-level block diagram of an example embodiment of training system 110 implemented using a network computing system. The training system 110 includes a plurality of client computers 920 (sometimes referred to herein simply as "clients") and a training server computer 910. Server 910 may itself be a central or a distributed server. A client computer 920 may be a laptop computer, a desktop computer, a cellular/VoIP handheld computer or smart phone, a tablet computer, distributed computer, or the like. An example system may have hundreds of thousands of clients. In an embodiment, the training server and/or each of the client computers can have the structure of FIG. 8, or any of its variations as described above. The client computers 920 communicate with the training server 910 to receive individuals for testing, and to report tested individuals back to the training server 910. The training server 910 maintains a server-centric experience-layered elitist pool 118, but in an embodiment, does not maintain any candidate individuals below layer $L_1$ of the elitist pool. New individuals are created by clients, both during initialization and by procreation, and they are not reported to the training server 910 until they have been tested on sufficient numbers of samples to qualify for the server's elitist pool 118. The number of individuals created by the clients 920 may vary depending on the memory size and the CPU processing power of the client. For example, in one embodiment, a client may have 1000 individuals for evaluation. Each client computer 920 further has a communication port to access one or more data feed servers 930, which retrieve and forward training samples from the training database 114 to the client computers 920. Alternatively, although not shown, the training samples may be supplied from data feed server 930 to the clients 920 via the training server 910.

Figure 10:
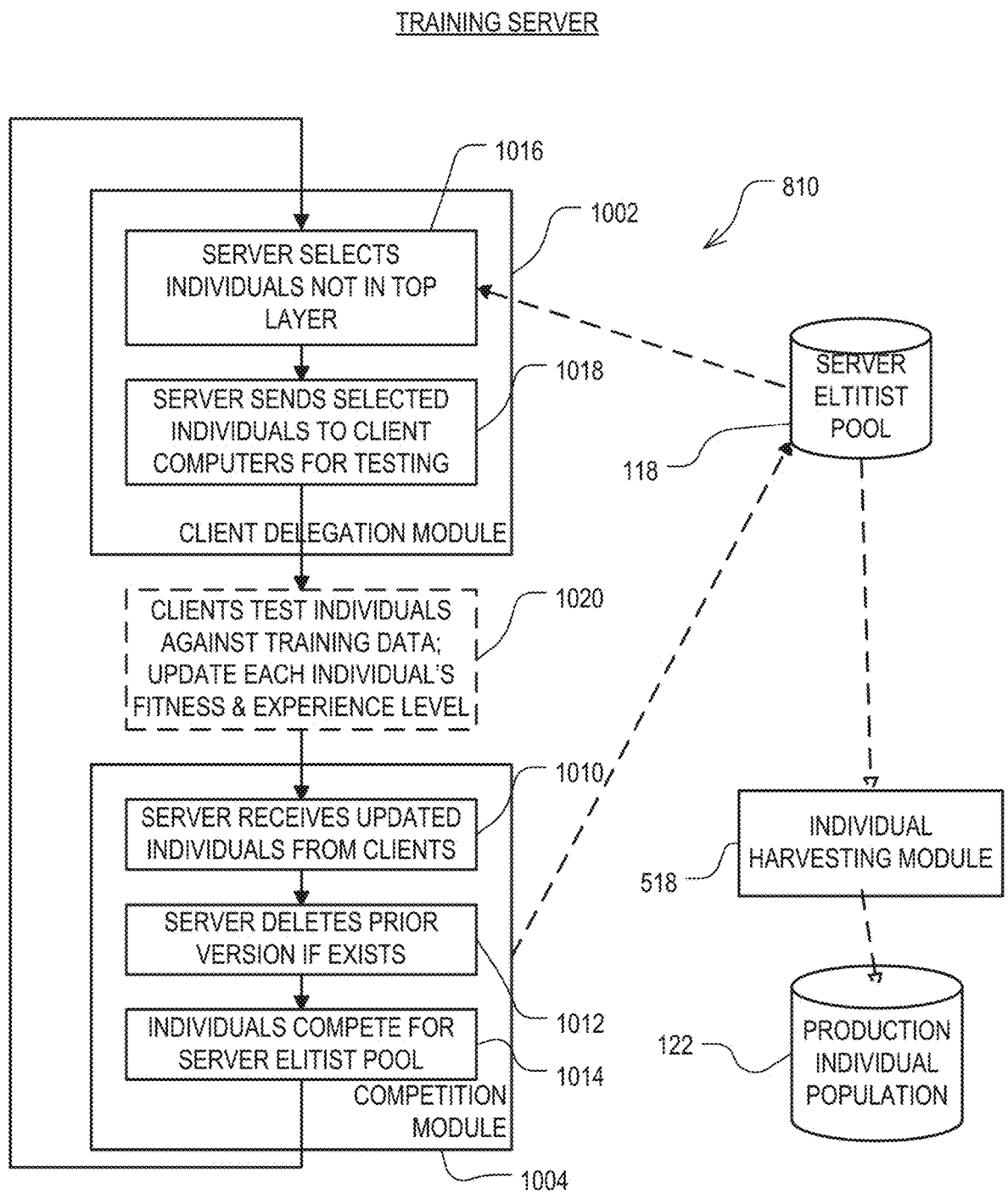
FIG. 10 illustrates modules that can be used to implement the functionality of training server of FIG. 8, according to an embodiment of the invention.

FIG. 10 illustrates various modules that can be used to implement the functionality of training server 910 (FIG. 9). Elitist pool 118 and production individual population database 122 are also shown in the drawing. As in the embodiment of FIG. 5, solid lines in FIG. 10 indicate process flow, and broken lines indicate data flow. The implementation variations mentioned above with respect to the embodiment of FIG. 5 apply to FIG. 10 as well.

In the client/server model enforces competition within its own server-centric elitist pool 118 when individuals are returned from clients. FIG. 10 illustrates various modules that can be used to implement the functionality of training server 910. Like the embodiment of FIG. 5, the training server 910 includes a competition module 1004. It also includes individual harvesting module 518, which may be same as in FIG. 5. It also includes individual testing and procreation functionality, but these are combined into a single client delegation module 1002 in FIG. 10. The client delegation module 1002 and the competition module 1004 constitute two sub-modules in an individual pool processor module (not shown specifically in FIG. 10). The FIG. 10 embodiment does not include a pool initialization module in the sense of FIG. 5, since as mentioned, the clients initialize their own individual pools.

Referring to FIG. 10, in step 1010, the competition module 1004 receives individuals from one or more of the client computers 920. These individuals may arrive asynchronously, if and when client computers have them available to transmit. Some individuals previously sent out for testing may never return. Individuals may arrive individually, or in bunches. If an arriving individual is new to the training server 910 (and, in some embodiments, also if the arriving individual is already known to the training server 910). At various times determined by competition module 1004, after at least one individual has arrived, competition module 1004 proceeds to step 1012 to begin a competition "event".

In step 1012, competition module 1004 determines whether each incoming individual is a new one, or a return of an individual that the server previously sent out for testing. This determination can be made on the basis of individual IDs 312 (FIG. 3). If the latter, then the training server 910 merges the newly received copy of the individual into the prior version in the server-centric elitist pool 118. In one embodiment, the merging step involves merely replacing the prior copy of the individual in the server-centric elitist pool 118, with the one newly received. In a variation of that embodiment, replacing may involve merely updating the experience level and the fitness estimation of the prior copy of the individual in the server-centric elitist pool 118.

In step 1014 the incoming individual (if new) or the updated individual (if merged) competes for its position in the server elitist pool 118. The same variations and rules of competition apply here as they do for the competition module 514 in the server-only model. That is the now-appropriate experience layer is full, the dominance estimate of the individuals in that experience layer is used to discard one or more individuals from the layer, as described in more detail with respect to FIGS. 6, 7A and 7B. An elitist pool minimum fitness policy can be applied here as well, based on a server-centric minimum fitness level.

In the client delegation module 1002, in step 1016, the server 910 selects individuals from the server-centric elitist pool 118, and sends them out to one or more clients 920 for further testing (step 1018). As in the server-only embodiment, the client delegation module 1002 is restricted from selecting for further testing individuals already in the top layer of the elitist pool 118. In one embodiment, the battery of trials that an individual is to undergo is dictated by the training server. In such an embodiment, the server-centric view of the battery is the same as the client-centric view of the battery. In another embodiment, the battery of trials that an individual is to undergo is left to the client to decide, and client may perform more than one battery of trials on the individual before returning it to the server. In the latter embodiment, the client has its own client-centric view of a testing battery.

In step 1020 the client machines 920 test the individuals against training data from the data feed server 930, and update each individual's fitness and experience level locally. Step 1020 is shown in broken lines in FIG. 10 because it is performed by clients rather than training server 910. At various subsequent times, the server 910 again receives back updated individuals from the clients in step 1010, and repeats the process of FIG. 10.

The operation of the client computers 920 is the same as that previously described with respect to FIGS. 5 and 6, with the exception that individuals are provided both by the pool initialization module 510, as well as from the training server 910. The candidate individual pool 116 in a client computer 920 is client-centric, and includes all candidate individuals being considered by the clients, including those that do not yet have sufficient experience to be considered for the elitist pool in the client computer. The candidate individual pool in the clients are nested experience layer-oriented as shown in FIG. 2, and for convenience, the experience layers in a client computer are sometimes designated herein with a top experience layer numbered CT rather than T, and with layers designated $CL_0$-$CL_{CT}$. The nested layers inside the experience layers in a client computer are sometimes designated herein as $CT_0$-$CT_{CN}$. None of the experience layer parameters in the client-centric individual pool, including the number of layers, need be the same as their corresponding parameters in other clients or in the server. Preferably the candidate individual pool 116 in the client computers 920 are implemented using linked lists, whereas the elitist pool 118 in the server 910 are implemented using a DBMS, both as previously described.

Unlike the single server embodiment, the individual testing module in the client computer 920 does not prevent further testing of individuals that have reached the top layer $CL_{CT}$ of the client-centric elitist pool 920. The individual harvesting module in a client computer 920 selects individuals only from the top layer $CL_{CT}$ of the client computer 920 for transmitting back to the server 910. Since the server 910 does not maintain any individuals that do not qualify for the server-centric elitist pool 118, the minimum experience level of the top layer $CL_{CT}$ in the client-centric elitist pool on each client computer 920 must be at least as high as the minimum experience level of the lowest layer $L_1$ of the elitist pool 118 of the training server 910. Preferably the minimum experience level of the top layer $CL_{CT}$ in the client-centric elitist pool on each client computer 920 is equal to the minimum experience level of the lowest layer $L_1$ of the elitist pool 118 of the training server 910.

Note that because of procreation on the client system 920, individuals may be sent up to the training server 910 which the training server 910 had never before seen. Such individuals are handled in step 1014 by requiring them to compete for their position in the server-centric elitist pool 118 of the training server 910. Note further that because of competition in the client computer 920, some individuals that the training server 910 sent to the client computer 920 for further testing will never be returned to the training server 910. In this case the prior copy of the individual, retained by the training server 910, remains in place in the elitist pool 118 of the training server 910 unless and until it is displaced through competition in the training server 910 (step 1014). Still further, note that an individual retained in the training server 910 after it has also been sent to a client 920 for further testing, may become displaced and deleted from the elitist pool 118 in the training server 910 through competition in the training server 910 (step 1014). In this case, if the same individual is returned by the client computer 920, the training server 910 simply ignores it.

Procreation

Figure 11:
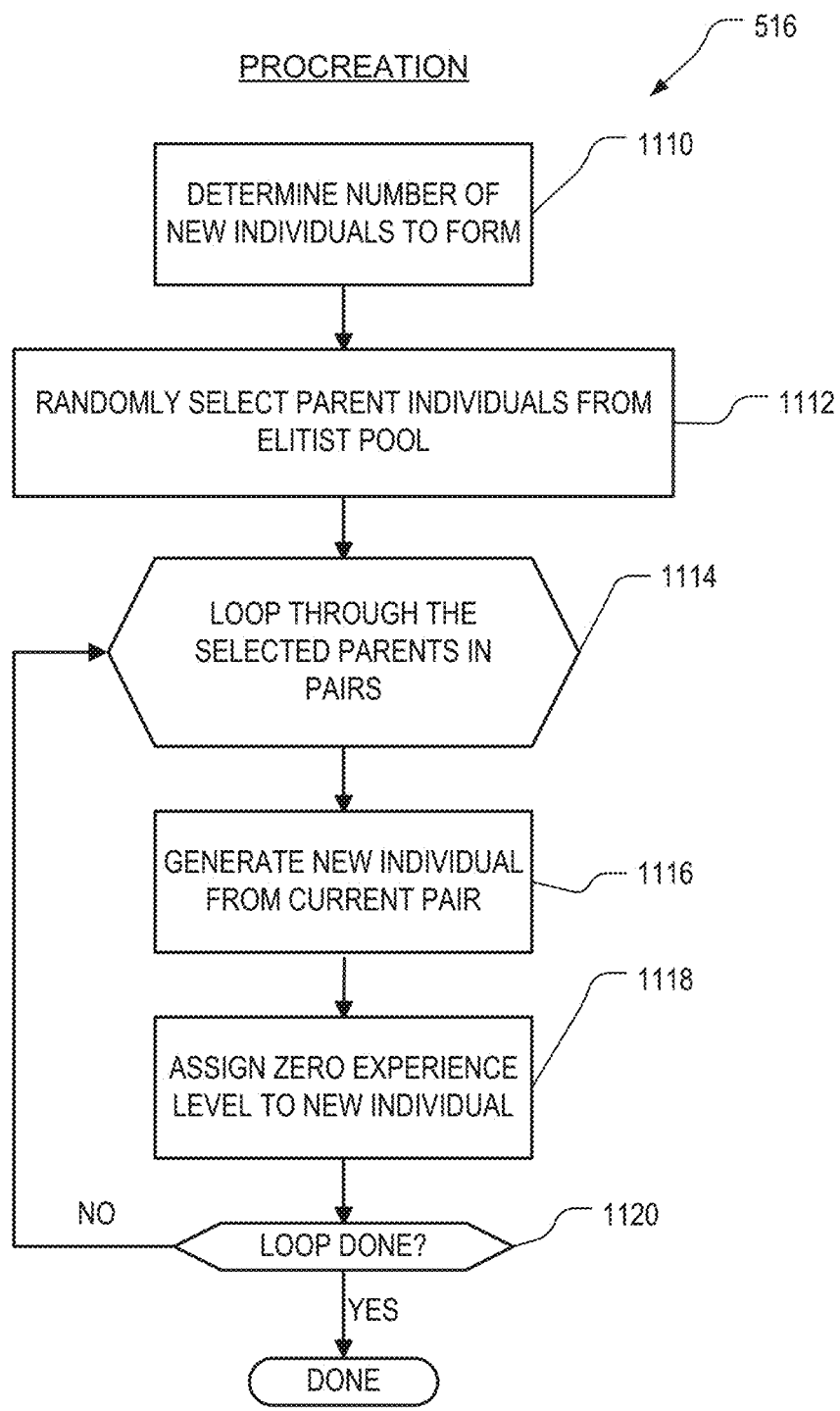
FIG. 11 is a flowchart of the procreation module in FIG. 5 according to an embodiment of the invention.

As mentioned, the procreation events that take place in procreation module 516. FIG. 11 is a flow chart illustrating an embodiment of this feature in more detail. Referring to FIG. 11, in step 1110 the procreation module 516 determines how many new individuals to form in the current procreation event. For example, the number in one embodiment is calculated as 5% of the total number of individuals in the elitist pool.

In step 1112, the procreation module 516 selects parent individuals from the elitist pool to use in the procreation process. Typically the individuals are selected randomly from throughout the elitist pool, though in an experience layered embodiment they might be selected only from one or more layers of the elitist pool.

In step 1114, the procreation module 516 begins a loop through the selected parents. Preferably parents are selected in pairs, and each new individual is formed from exactly two parents. In another embodiment, however, new individuals can be formed from a single parent individual, or from three or more parent individuals. In general, a "set" of one or more parents is used in the formation of each new individual by procreation.

In step 1116, a new individual is formed from the current set of parents.

Any method of procreation can be used, such as those set forth elsewhere herein. In step 1118 a zero experience level is assigned to the new individual, and in step 1120 it is determined whether there are more sets of parents selected to procreate. If so, then procreation module 516 returns back to step 1114 to generate another new individual by procreation.

Alternate Embodiments

There are many embodiments evolving individuals in an evolutionary algorithm. The approach described herein may be implemented by any of the following embodiments.

In an embodiment, the evolutionary algorithm is distributed across multiple computers. The computers may be assigned a role of coordinator, mid-level coordinator, or evolutionary engine in which an evolutionary engine initializes, procreates, tests, and scores individuals, and coordinators compare individuals across evolutionary engine. This is a federated approach. See, for example, the above-incorporated U.S. Pat. No. 9,466,023 (GNFN 3100-1).

In an embodiment, the number of training data samples or an individual is tested against is tracked in an indication of experience level, and only those individuals with similar experience levels are permitted to compete with each other for a place in the candidate pool. See, for example, the above-incorporated U.S. Pat. No. 8,909,570 (GNFN 3010-1). The individuals selected as parents for procreation are selected from among the best scoring of the most experienced individuals.

In an embodiment, parents involved in procreation are removed from the candidate pool, and in other embodiments, they remain in the candidate pool.

In an embodiment, an individual's fitness score may be retained and further refined across generations as an individual is tested against new training data. In an embodiment, previous fitness scores are not used and a new fitness score is determined based only on the performance of the testing data of the current generation.

In an embodiment, an individual can also contain or identify a history of the separate fitness trials to which the individual has been subjected. Such a fitness history can be used to avoid re-testing the individual on the same data sample, or can be used to remove the effect of duplicate tests performed on an individual in different testing batteries before merging the fitness evaluations. It can also be used to help diversify the candidate pool, by comparing or weighting individuals not only on their overall fitness evaluations, but also on the way they reached their overall fitness evaluations. Fitness trial history also can be taken account when filtering the final pool of individuals for selection for deployment.

Many other variations will be apparent to the reader.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "indicate" is used herein to mean the same as "identify".

Also as used herein, a given event or value is "responsive" to a predecessor event or value if the predecessor event or value influenced the given event or value. If there is an intervening processing element, step or time period, the given event or value can still be "responsive" to the predecessor event or value. If the intervening processing element or step combines more than one event or value, the signal output of the processing element or step is considered "responsive" to each of the event or value inputs. If the given event or value is the same as the predecessor event or value, this is merely a degenerate case in which the given event or value is still considered to be "responsive" to the predecessor event or value. "Dependency" of a given event or value upon another event or value is defined similarly.

Applicants hereby disclose in isolation each individual feature described herein and each combination of two or more such features, to the extent that such features or combinations are capable of being carried out based on the present specification as a whole in light of the common general knowledge of a person skilled in the art, irrespective of whether such features or combinations of features solve any problems disclosed herein, and without limitation to the scope of the claims. Applicants indicate that aspects of the present invention may consist of any such feature or combination of features. In view of the foregoing description it will be evident to a person skilled in the art that various modifications may be made within the scope of the invention.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. For example, dominance estimate for individuals in candidate individual pool 116 can in some embodiments be made available for external retrieval and/or analysis through the use of an API (not shown). As another example, dominance estimate can be used as a measure of convergence of the candidate individual pool. For example, in one embodiment, a system periodically computes an Average Fitness Leap Per Ancestor Count Increment of the candidate population. If the rate of change of such a measure is in continual decline down to a certain threshold, convergence is indicated and further procreation or evaluation of the population is terminated. Further, and without limitation, any and all variations described, suggested or incorporated by reference in the Background section or the Cross References section of this patent application are specifically incorporated by reference into the description herein of embodiments of the invention. In addition, any and all variations described, suggested or incorporated by reference herein with respect to any one embodiment are also to be considered taught with respect to all other embodiments. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A computer-implemented method for discovering optimal solutions to a problem defined based on a provided fitness function and provided training data, comprising the steps of:
   i. providing a computer system having a memory having a candidate pool database identifying a pool of candidate individuals, each candidate individual identifying a potential solution to the problem, each candidate individual further having associated therewith an indication of a respective fitness estimate;
   ii. a computer system testing individuals from the pool of candidate individuals against a portion of the training data;
   iii. a computer system updating the fitness estimates for selected ones of individuals tested, in dependence upon the results of such testing, wherein the fitness estimate for each candidate individual in the pool is determined by the computer system based on a predetermined performance measure that is specific to the problem, the computer system calculating the fitness estimate in accordance with the following:

$$\text{fitness estimate} = \frac{\sum_{i=1}^{n} \text{performance measure}_i}{n}$$

wherein performance measure$_i$ is each candidate individual's performance measure when tested on a data sample i from the training data, and n is the number of data samples on which each candidate individual has been tested;

iv. a computer system determining a domination estimate for (x) individuals from the pool of candidate individuals relative to other (y) individuals in the pool in accordance with the following function $$(x,y)=(f(x)-f(y))-w \cdot d(b(x),b(y))$$

wherein f(x)−f(y) is the fitness estimate difference between individuals x and y, d(b(x),b(y)) is the behavior difference between individuals x and y, and w is a scaling parameter;

v. a computer system selecting individuals for discarding from the pool of candidate individuals, in dependence upon their domination estimate, wherein the non-discarded candidate individuals are stepping stone candidate individuals;

vi. procreating by the computer system additional candidate individuals using at least the stepping stone candidate individuals in accordance with predetermined procreation rules, wherein the additional candidate individuals are subjected to testing against a portion of the training data, assigned estimate fitness estimates and subjected to domination estimate comparison vii. repeating steps ii. to vi. until an elitist pool of candidate individuals representing optimal solutions is achieved.

2. The method of claim 1, wherein testing individuals from the pool of candidate individuals against a portion of the training data includes identifying a behavioral value of the individual when tested against the portion of the training data, according to a predefined measure of behavior.

3. The method of claim 1, wherein the domination estimate between the pair of individuals in the pool is defined such that an increase in the fitness estimate difference between the pair of individuals increases their domination estimate.

4. The method of claim 1, wherein the domination estimate between the pair of individuals in the pool is defined such that an increase in the behavior difference between the pair of individuals decreases their domination estimate.

5. The method of claim 1, wherein estimating a domination estimate for individuals from the pool of candidate individuals relative to other individuals in the pool comprises estimating the domination estimate between each pair of individuals in the pool.

6. The method of claim 1, wherein selecting individuals for discarding from the pool of candidate individuals in dependence upon their domination estimate comprises building a retention set of N>0 individuals to retain and discarding from the pool all individuals in the pool which are not in the retention set, wherein building the retention set comprises:

adding to the retention set a number NO of individuals that are not dominated by any other individuals in the pool, NO being the lesser of N and the number of individuals in the pool that are not dominated by any other individuals in the pool; and for i incrementing from 1 until the number of individuals in the retention set reaches N, adding to the retention set Ni individuals that are dominated by individuals in the retention set but not by any other individuals in the pool.

7. The method of claim 6, wherein in the last iteration of adding to the retention set Ni individuals, i is equal to a final value p, wherein after the (p−1)'th iteration, P>1 of the individuals in the pool of candidate individuals are dominated by individuals in the retention set but not by any other individuals in the pool, the P individuals constituting a p'th subset, and wherein adding to the retention set Np individuals comprises selecting the Np individuals from among the individuals in the p'th subset in dependence upon both their relative fitness and the relative similarity of their behavior.

8. The method of claim 7, wherein testing individuals from the pool of candidate individuals against a portion of the training data includes identifying a behavioral value of the individual when tested against the portion of the training data, according to a predefined measure of behavior, and wherein selecting the Np individuals from among the individuals in the p'th subset comprises iteratively, until the number of individuals in the p'th subset reaches Np, removing from the p'th subset the less fit of two individuals in the p'th subset which are most similar in their behavioral values.

9. A computer-implemented system for discovering optimal solutions to a problem defined based on a provided fitness function and provided training data, comprising:

a memory storing a candidate pool database identifying a pool of candidate individuals, each candidate individual identifying a potential solution to the problem, each candidate individual further having associated therewith an indication of a respective fitness estimate;

a processing unit which:

i. tests individuals from the pool of candidate individuals against a portion of the training data;

ii. updates the fitness estimates for selected ones of individuals tested, in dependence upon the results of such testing, wherein the fitness estimate for each candidate individual in the pool is determined by the computer system based on a predetermined performance measure that is specific to the problem, the computer system calculating the fitness estimate in accordance with the following:

$$\text{fitness estimate} = \frac{\sum_{i=1}^{n} \text{performance measure}_i}{n}$$

wherein performance measure$_i$ is each candidate individual's performance measure when tested on a data sample i from the training data, and n is the number of data samples on which each candidate individual has been tested;

iii. determines a domination estimate for (x) individuals from the pool of candidate individuals relative to other (y) individuals in the pool in accordance with the following function $$(x,y)=(f(x)-f(y))-w \cdot d(b(x),b(y))$$

wherein f(x)−f(y) is the fitness estimate difference between individuals x and y, d(b(x),b(y)) is the behavior difference between individuals x and y, and w is a scaling parameter;

iv. selects individuals for discarding from the pool of candidate individuals, in dependence upon their domination estimate, wherein the non-discarded candidate individuals are stepping stone candidate individuals;

v. procreates additional candidate individuals using at least the stepping stone candidate individuals in accordance with predetermined procreation rules, wherein the additional candidate individuals are subjected to testing against a portion of the training data, assigned estimate fitness estimates and subjected to domination estimate comparison vi. repeats steps i. to v. until an elitist pool of candidate individuals representing the optimal solutions is achieved.

10. The system of claim 9, wherein in testing individuals from the pool of candidate individuals against a portion of the training data, the processing unit identifies a behavioral value of the individual when tested against the portion of the training data, according to a predefined measure of behavior.

11. The system of claim 9, wherein an increase in the fitness estimate difference between the pair of individuals increases their domination estimate.

12. The system of claim 9, wherein an increase in the behavior difference between the pair of individuals decreases their domination estimate.

13. The system of claim 9, wherein in estimating a domination estimate for individuals from the pool of candidate individuals relative to other individuals in the pool, the processing unit estimates the domination estimate between each pair of individuals in the pool.

14. The system of claim 9, wherein in selecting individuals for discarding from the builds a retention set of N>0 individuals to retain and discards from the pool all individuals in the pool which are not in the retention set, wherein building the retention set comprises:

adding to the retention set a number NO of individuals that are not dominated by any other individuals in the pool, NO being the lesser of N and the number of individuals in the pool that are not dominated by any other individuals in the pool; and for i incrementing from 1 until the number of individuals in the retention set reaches N, adding to the retention set Ni individuals that are dominated by individuals in the retention set but not by any other individuals in the pool.

15. The system of claim 14, wherein in the last iteration of adding to the retention set Ni individuals, i is equal to a final value p, wherein after the (p−1)'th iteration, P>1 of the individuals in the pool of candidate individuals are dominated by individuals in the retention set but not by any other individuals in the pool, the P individuals constituting a p'th subset, and wherein adding to the retention set Np individuals comprises selecting the Np individuals from among the individuals in the p'th subset in dependence upon both their relative fitness and the relative similarity of their behavior.

16. The system of claim 15, wherein testing individuals from the pool of candidate individuals against a portion of the training data includes identifying a behavioral value of the individual when tested against the portion of the training data, according to a predefined measure of behavior, and wherein selecting the Np individuals from among the individuals in the p'th subset comprises iteratively, until the number of individuals in the p'th subset reaches Np, removing from the p'th subset the less fit of two individuals in the p'th subset which are most similar in their behavioral values.

17. A non-transitory computer readable medium having stored thereon a plurality of instructions which when executed by a processing unit cause the processing unit to:

i. provide a candidate pool database identifying a pool of candidate individuals, each candidate individual identifying a potential solution to a provided problem which is defined based on a provided fitness function and provided training data, each candidate individual further having associated therewith an indication of a respective fitness estimate;

ii. test individuals from the pool of candidate individuals against a portion of the training data;

iii. update the fitness estimates for selected ones of individuals tested, in dependence upon the results of such testing, wherein the fitness estimate for each candidate individual in the pool is determined by the computer system based on a predetermined performance measure that is specific to the problem, the computer system calculating the fitness estimate in accordance with the following:

$$\text{fitness estimate} = \frac{\sum_{i=1}^{n} \text{performance measure}_i}{n}$$

wherein performance measure$_i$ is each candidate individual's performance measure when tested on a data sample i from the training data, and n is the number of data samples on which each candidate individual has been tested;

iv. determine a domination estimate for (x) individuals from the pool of candidate individuals relative to other (y) individuals in the pool in accordance with the following function $$(x,y)=(f(x)-f(y))-w \cdot d(b(x),b(y))$$

wherein f(x)−f(y) is the fitness estimate difference between individuals x and y, d(b(x),b(y)) is the behavior difference between individuals x and y, and w is a scaling parameter; and v. select individuals for discarding from the pool of candidate individuals, in dependence upon their domination estimate, wherein the non-discarded candidate individuals are stepping stone candidate individuals;

vi. procreate additional candidate individuals using at least the stepping stone candidate individuals in accordance with predetermined procreation rules, wherein the additional candidate individuals are subjected to testing against a portion of the training data, assigned estimate fitness estimates and subjected to domination estimate comparison vii. repeat steps ii. to vi. until an elitist pool containing an optimal set of individuals is achieved.

18. A computer-implemented data mining system, for use with a data mining training database containing training data and for further use in selecting a diverse and optimal set of individuals, comprising:

a memory storing a candidate pool database identifying a pool of candidate individuals, each candidate individual identifying a plurality of conditions and at least one corresponding proposed output in dependence upon the conditions, each candidate individual further having associated therewith an indication of a respective fitness estimate;

means for testing individuals from the pool of candidate individuals against a portion of the training data;

means for updating the fitness estimates for selected ones of individuals tested, in dependence upon the results of such testing, wherein the fitness estimate for each candidate individual in the pool is determined by the computer system based on a predetermined performance measure that is specific to the problem, the computer system calculating the fitness estimate in accordance with the following:

$$\text{fitness estimate} = \frac{\sum_{i=1}^{n} \text{performance measure}_i}{n}$$

wherein performance measure$_i$ is each candidate individual's performance measure when tested on a data sample i from the training data, and n is the number of data samples on which each candidate individual has been tested;

means for determining a domination estimate for (x) individuals from the pool of candidate individuals relative to other (y) individuals in the pool in accordance with the following function $(x,y)=(f(x)-f(y))-w \cdot d(b(x),b(y))$ wherein f(x)–f(y) is the fitness estimate difference between individuals x and y, d(b(x),b(y)) is the behavior difference between individuals x and y, and w is a scaling parameter;

means for selecting individuals for discarding from the pool of candidate individuals, in dependence upon their domination estimate;

means for procreating additional candidate individuals using at least the stepping stone candidate individuals in accordance with predetermined procreation rules, wherein the additional candidate individuals are subjected to testing against a portion of the training data, assigned estimate fitness estimates and subjected to domination estimate comparison;

repeating steps of testing, updating, determining, selecting and procreating until an elitist pool containing an optimal set of individuals is achieved.

* * * * *